United States Patent
Viscomi et al.

(10) Patent No.: US 7,367,802 B2
(45) Date of Patent: May 6, 2008

(54) BARRIER FREE MATRIX BAND WITH FLASH GUARD

(76) Inventors: Dominic Anthony Viscomi, 1868 Felicity La., Hellertown, PA (US) 18055; Brian David Viscomi, 500 Central Ave., Union City, NJ (US) 78087

( * ) Notice: Subject to any disclaimer, the term of this patent is extended or adjusted under 35 U.S.C. 154(b) by 390 days.

(21) Appl. No.: 11/092,490

(22) Filed: Mar. 29, 2005

(65) Prior Publication Data
US 2006/0084029 A1    Apr. 20, 2006

Related U.S. Application Data

(60) Provisional application No. 60/619,524, filed on Oct. 18, 2004, provisional application No. 60/612,989, filed on Sep. 25, 2004.

(51) Int. Cl.
*A61C 5/04* (2006.01)
(52) U.S. Cl. ...................................... 433/39
(58) Field of Classification Search ............ 433/38–40, 433/149
See application file for complete search history.

(56) References Cited

U.S. PATENT DOCUMENTS

| | | | |
|---|---|---|---|
| 1,133,379 A * | 3/1915 | Hollingsworth | 433/39 |
| 2,591,744 A | 4/1952 | Tofflemire | |
| 4,024,643 A | 5/1977 | Eisenberg | |
| 4,781,583 A * | 11/1988 | Lazarus | 433/39 |
| 5,330,353 A | 7/1994 | Waverin | |
| 6,350,122 B1 * | 2/2002 | Meyer | 433/39 |
| 6,509,540 B1 * | 1/2003 | Summer et al. | 219/91.2 |
| 6,736,639 B1 | 5/2004 | Summer | |
| 7,037,109 B1 * | 5/2006 | Viscomi et al. | 433/39 |
| 7,214,058 B2 * | 5/2007 | Summer | 433/39 |
| 2005/0221255 A1 * | 10/2005 | Haraden et al. | 433/39 |
| 2005/0287491 A1 * | 12/2005 | Slone | 433/39 |
| 2006/0084036 A1 * | 4/2006 | Boston | 433/215 |

FOREIGN PATENT DOCUMENTS

| | | |
|---|---|---|
| DE | 195 46 454 | 6/1997 |
| WO | WO 2005/023135 | 3/2005 |

* cited by examiner

*Primary Examiner*—Ralph A. Lewis

(57) ABSTRACT

A dental matrix band (1) having a brace extrusion window (4), a flash guard (14) and guard brace (22) which fold to articulate into a conventional Tofflemire-like matrix band shape. The flash guard (14) is secured by the guard brace (22) against the brace extrusion window 4. This serves as a barrier to temporarily block a restorative substance from passing into an inter-proximal space. After cutting a connecting severance junction (30), the flash guard (14) is removed via a removal tab (16) and aperture (18). The restorative material is then displaced to created direct contact with an adjacent inter proximal surface through the window 4. After polymerization, a series of linearly aligned notches (28a,b,c,d), superior window notches (8a,b), inferior window notch (10a,b) and gingival notch (12a,b) permit a vertical bisection split through the matrix (1) conjoined aperture(25). This facilitates the matrix (1) removal from a cured contact point.

14 Claims, 31 Drawing Sheets

BARRIER FREE MATRIX BAND WITH FLASH GUARD

CROSS-REFERENCE TO RELATED APPLICATION

THIS APPLICATION CLAIMS THE BENEFIT OF PROVISIONAL PATENT APPLICATIONS Ser. No. 60/612,989, FILED Sep. 25, 2004; AND Ser. No. 60/619524, FILED Oct. 18, 2004, BY THE PRESENT INVENTORS.

FEDERALLY SPONSORED RESEARCH

Not Applicable

SEQUENCE LISTING OR PROGRAM

Not Applicable

BACKGROUND OF THE INVENTION—FIELD OF INVENTION

This invention relates to the field of dentistry, specifically an improved matrix system for posterior class II composite resin dentistry.

BACKGROUND OF THE INVENTION

Complex cavity preparations of posterior teeth require a supporting or retaining wall to contain the restorative materials within the confines of the tooth until the filling material achieves a setting or hardening state. The wall that dentists have traditionally used is an elongated flexible strip called a matrix band. Previous matrix bands were conceived to deal with the traditional metal-based, or amalgam filling materials. They availed of amalgam's physical properties of multi-directional expansion through its hardening phase. Therefore, retaining mediums separating the inter-proximal areas between a prepared tooth and its abutting neighbor could be successfully removed while ensuring that positive tooth to filling contact would ensue.

The matrix band disclosed in U.S. Pat. No. 2,591,744 to Tofflemire is the industry standard and staple matrix band. It encircled the tooth and provides a rigid wall with which to contain the amalgam restorative material. Although a separating wall remains until the filling material reached its hardening phase, amalgam's expansion capabilities plus moderate inter-proximal wedging tooth separation maintained the desired restoration to tooth contact upon removal of the barrier wall. Thus, potential inter-proximal food impaction and subsequent gingival or gum irritation are eliminated. We shall, however, demonstrate the band's short-comings with alternative and current restorative materials.

The advent of tooth colored restorative materials, namely composite resins, is in response to amalgam's questionable toxicity due to its mercury component, and the demand for esthetics. However, one of the major inadequacies of composite resin materials is the antithesis of amalgam's forte, that is, it contracts rather than expand while hardening, or polymerizing. Conventional matrix retaining systems therefore allowed for an inter-proximal gap to remain upon removal of the matrix band. This exposed the inter-proximal area to the aforementioned pathology, that is, food impaction and gum irritation. Prior arts' remedy for this introduced a thinner metal matrix band to reduce the thickness of the separating wall, and non-metal or Mylar strips, in conjunction with enhanced wedging or separation between the teeth. This potentially allows for more filling material to be introduced into the cavity preparation to compensate for anticipated shrinkage. These attempts proved to be not without limitations. Mylar strips lack sufficient rigidity, and their placement presented ergonomic challenges. The introduction of thinner metal matrix bands still required a barrier wall to remain during the setting phase, and thus did not ensure a consistent desired inter-proximal contact. These present as a major disadvantage to a technique sensitive restorable material. In addition, present day composite resins have dual-cure capabilities. That is, the application of the curing light medium allows the resin to self-cure or harden and lessens its dependency on the light. This feature obviates the need for transparent retaining barriers and allows the dentist to use standard metal matrix retaining apparatuses.

Another matrix system presents a band with a plastic, or celluloid based inter-proximal contact area, attached between adjacent metal lateral extensions. Plastic's inherent lack of rigidity complicates the band's insertion, and allows for the unavoidable escape of filling material into unwanted areas. In addition, composite resin's dual curing properties eliminate the need for transparency in a matrix system. The band can also contraindicate the employment of a rubber dam or isolation barrier often essential for successful placement of current moisture sensitive composite resins. Furthermore, the band's retaining wall that is present at the completion of the filling's condensation and polymerization can, upon removal, result in an undesirable gap, or open contact. In addition, the band's fabrication requirements of micro-etching and epoxy adhesives to conjoin the segments can add considerably to the production costs of an essentially disposable, single use device.

Another matrix presents a longitudinally split dental matrix band with a windowed opening at the contact area. This embodiment allows for extrusion of the compacted composite resin to abut directly to the adjacent tooth. However, the band's window, which is disjoined on one side, can contribute to unpredictable filling overflow, with subsequent contour and finishing challenges. This contraindicates multi-surface tooth restorations. Also, the window configuration of the band presents engagement with the polymerized resin to the extent that band removal may lacerate fragile gingival tissue thus contaminating the field of operation and contributing to unnecessary post-operative patient discomfort. Furthermore, the band's tension producing concept possesses ergonomic drawbacks presenting the clinician with insertion challenges in the posterior regions of the oral cavity. Engagement of this tension apparatus may also conflict with usage of the required rubber dam isolation.

Another band presents a matrix with two essential elements. The first, being an area of matrix that is hammered thin to coincide with the prepared aspect of a tooth. The other element is a large hole or aperture to coincide with the opposite side of the prepared proximal surface. The idea is to have as minimal material as possible but still have a permanently fixed barrier between the tooth preparation and the abutting proximal surface of the next tooth. The hole functions to minimize tooth separation on the opposite side of the prepared tooth helping to attain better contact upon polymerization. Several problems present with this matrix. First, the presence of a barrier as with all other conventional matrices still presents as an impediment to contact. Secondly, the thinned out barrier is not only permanently in place, but also sufficiently delicate as to make it difficult to insert in tight proximal operative scenarios. Additionally, the hole that is to coincide with the opposite side of the prep is also sufficiently weak with very little supportive metal to keep it from crumpling in tight proximal cases. It is also questionable whether fifteen thousandths of thickness removed from a matrix will significantly aid in tooth separation. Conclusively, this matrix presents as a conventional barrier similar to other matrices, though thinner in the contact area, the matrix still employs a fixed barrier that can result in open contact.

BACKGROUND OF INVENTION OBJECTS AND ADVANTAGES

Accordingly, several objects and advantages of the present patent application of Dominic A. Viscomi and Brian D. Viscomi for the Barrier Free Matrix Band with Flash Guard are:

(a) Band features allow for predictable and anatomically desirable inter-proximal contact.

(b) Functional attributes permit the replication of natural tooth contours and contact points.

(c) The band design eliminates occurrence undesirable inter-proximal flash.

(d) Band configuration permits for simultaneous multiple tooth surface restorations.

(e) Unique features minimize the restorative finishing process.

(f) The unique features dramatically increase the restorative success rate.

(g) Integrated feature saves significant chair side time.

(h) Removal system ensures that the polymerized composite extrusion will not sustain damage.

(i) Band removal is atraumatic to sensitive gingival tissue.

(j) Dual-purpose design allows for usage of both composite and amalgam restorative materials.

(k) Band is compatible with rubber dam isolation and moisture control barrier devices.

(l) Implementation of traditional band design does not require the use of specialized instruments or retainers.

(m) Predictable restoration to tooth inter-proximal contact allows for increased operator productivity.

Further objects and advantages are for the band to be readily incorporated into standard operative techniques while being compatible with existing chair-side armamentarium. The matrix band eliminates the need for multiple matrix retaining systems thus providing economies of purchase. Still further objects and advantages will become apparent from a consideration of the ensuing description and drawings.

SUMMARY OF THE INVENTION

In accordance with the present invention, a dental matrix band comprises flexible body, at least one aperture in the body, a flat flexible guard to cover and temporarily prevent the passage of a restorative material through the aperture and an integrated system to bi-laterally split the matrix band through the aperture.

DRAWINGS—FIGURES

Figure 1A:
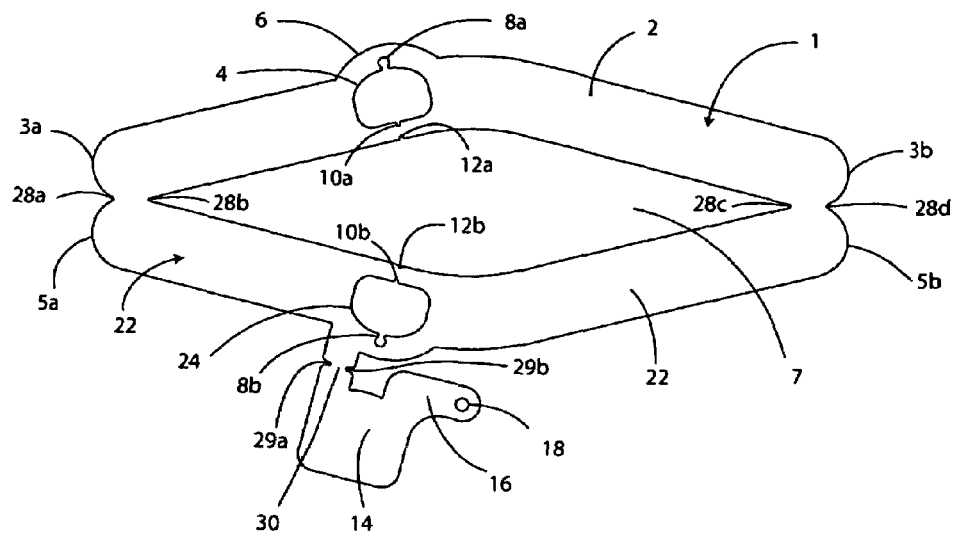
FIGS. 1A to 1C shows one unarticulated and two articulated views of a preferred embodiment MO/DO single surface matrix with two apertures, aperture associated separation notches, a mirrored guard brace and a connected flash guard with guard removal aperture.

| DRAWINGS - LIST OF REFERENCE NUMERALS | | | |
|---|---|---|---|
| 1 | matrix band | 2 | brace |
| 3(a) | brace left end | 3(b) | brace right end |
| 4 | left brace extrusion window | 4(a) | right brace extrusion window |
| 5(a) | guard brace left end | 5(b) | guard brace right end |
| 6 | left brace bridge | 6(a) | right brace bridge |
| 7 | diamond shaped aperture | | |
| 8(a) | left brace superior window notch | 8(c) | right brace superior window notch |
| 8(b) | left guard brace superior window notch | 8(d) | right brace superior window notch |
| 10(a) | left brace inferior window notch | 10(b) | left guard brace inferior window notch |
| 10(c) | right brace inferior window notch | 10(d) | right guard brace inferior window notch |
| 12(a) | left brace gingival notch | 12(b) | left guard brace gingival notch |
| 12(c) | right brace gingival notch | 12(d) | right guard brace gingival notch |
| 14 | left flash guard | 14(a) | right flash guard |
| 16 | left guard removal tab | 16(a) | right guard removal tab |
| 18 | left removal aperture | 18(a) | right removal aperture |
| 20 | tab junction | 22 | guard brace |
| 23(a) | left brace gingival extension | 23(b) | left guard brace gingival extension |
| 23(c) | right brace gingival extension | 23(d) | right guard brace gingival extension |
| 24 | left guard brace extrusion window | 24(a) | right guard brace extrusion window |
| 26(a) | right guard brace securing tab | 26(b) | left guard brace securing tab |
| 28(a) | left exterior band folding notch | 28(b) | left interior band folding notch |
| 28(c) | right interior band folding notch | 28(d) | right exterior band folding notch |
| 29(a) | left flash guard left folding notch | 29(b) | left flash guard right folding notch |
| 29(c) | right flash left right folding notch | 29(d) | right flash guard right folding notch |
| 30 | left severance junction | 30(a) | right severance junction |
| 31 | left-U-shaped folding notch | 31(a) | right-U-shaped folding notch |
| 32 | left brace superior buccal lingual severance junction | 32(a) | right brace superior buccal lingual severance junction |
| 34 | left brace superior buccal-lingual extension | 34(a) | right brace superior buccal lingual extension |
| 35 | left guard brace inferior buccal-lingual extension | 35(a) | right guard brace inferior buccal-lingual extension |
| 36(a) | left brace retainer grip extension | 36(b) | left guard brace retainer grip extension |
| 36(c) | right brace retainer grip extension | 36(d) | right guard brace right retainer grip extension |
| 38 | left guard brace adhesive application | 38(a) | right guard brace adhesive application |
| 39 | brace adhesive application left side | 39(a) | brace adhesive application right side |
| 40 | matrix retainer | 41 | contoured metal section |
| 42 | prepped first tooth | 44 | second tooth |
| 46 | wedge | 48 | composite resin |
| 50 | condensing instrument | 52 | shaping instrument |
| 54 | probe | 56 | scissors |
| 58 | evacuation apparatus | 60 | resin penetration |
| 62 | resin displacement | 64 | inter-proximal contact point |
| 66 | preparation box | 68 | polymerizing light |

-continued

DRAWINGS - LIST OF REFERENCE NUMERALS

| 70 | hand piece | 72 | progressive retainer tightening |
| 74 | inferior matrix band separation | 76 | finger |

DETAILED DESCRIPTION FIG. 1 PREFERRED EMBODIMENT

FIG. 1A (front view unarticulated) is a preferred embodiment of the present invention. The matrix band 1 is a flexible, mirrored band design, with a diamond-like shape. The matrix 1 can be die stamped, laser cut, chemically etched, or machine cut into configuration. The matrix band 1 may be fabricated from a biocompatible material such as stainless steel, plastic, or other semi-rigid material. Preferably, the matrix band is fabricated from a single piece of stainless steel uniformly thick. For stainless steel, the thickness of matrix bands will generally vary from 0.0010 inches to 0.0015 inches and preferably will be 0.0010 inches.

As shown in FIG. 1A, the matrix band is comprised of a body. Preferably the body has (a), a first portion, which is a boomerang shaped brace 2 having a left end 3a, and a right end 3b, and (b) a second portion, which is a boomerang-shaped guard brace 22, having a left end 5a and a right end 5b. Each of said left ends and right ends join to form a diamond shaped opening or aperture 7. Preferably, the body is formed from a single piece of material, so that the connection between first and second body portions at the left and right ends is accomplished by the forming. However, although not economical, such connections could be accomplished by forming separate body portions and joining them together with conventional means such as welding, gluing or crimping.

Located within the medial region of the brace 2 interior is a hole, aperture, or extrusion window 4. The window 4 is shaped and sized to position within the inter-proximal space between the contact areas of a prepped first tooth 42 and a second tooth 44 (FIG. 16). Preferably, the window 4 shape has three straight areas, two radiated corners, and a curved, semi-elliptical superior aspect. The three straight aspects, two lateral, one inferior assume a rectangular dimension to approximate the box shape typical of class II inter-proximal preparations. The curved superior window 4 border is contiguous to a superiorly positioned bulge, rounded arch, or bridge 6 that extends superiorly to the restorative area. The window 4 configuration and size allows for minimal interference with a restorative area. This lessens the potential occurrence of window 4 associated impressions (formed in the uncured composite resin 48) and related inter-proximal irregularities.

Figure 1B:
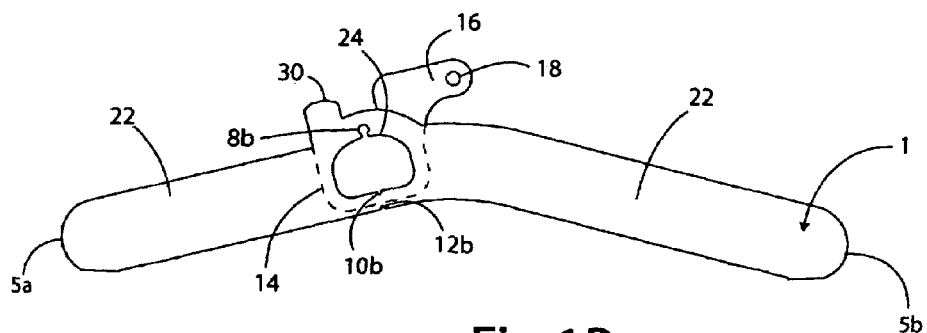
Figure 1C:
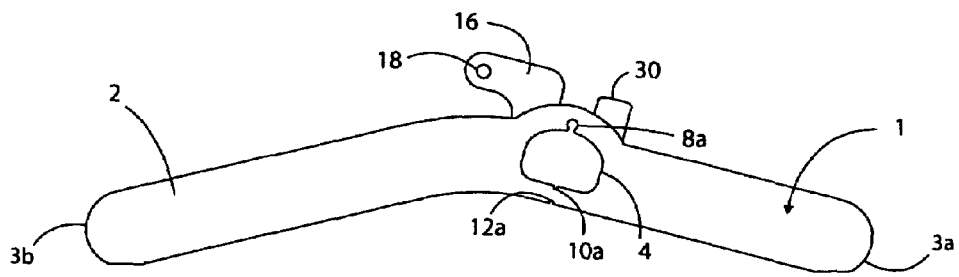

Preferably, positioned directly above the window 4 is a rounded arch of continuous material or bridge 6. The bridge 6 compensates for the height of the arched upper extrusion window's 4 border (would extend beyond the confines of the brace 2 border if the bridge 6 were not present). Additionally, the bridge 6, (when the articulated band FIGS. 1B-1C is placed on a tooth) rises above the occlusal surface or marginal ridge when placed upon a tooth. Integrated on the extreme superior and inferior window 4 borders are two wedge-shaped cutouts or notches 8a, 10a. The superior window notch 8 extends upward into the expanse of the bridge 6. It is viewable above the occlusal surfaces of two abutting teeth when the matrix band 1 is articulated as described below and placed inter-proximally between them. This notch 8a is also conspicuously sized and shaped to permit enhanced visibility for band placement and band removal. The inferior window notch 10a resides directly below the superior window notch 8a and is smaller in size than the superior window notch 8a. When the articulated matrix band 1 is placed inter-proximally, the inferior window notch 10a is obscured and not visible. Positioned a short distance below the inferior window notch 10a is a third notch or gingival notch 12a that is associated with the inferior border of the brace 2 (has no association with the extrusion window 4). All three of these notches are positioned in a vertical, linear alignment with regard to one another. The linear notch alignment bi-sects the extrusion window 4.

Guard brace 22 is a mirror-like attachment to the brace 2 and is identical in size and shape. The combined visual result of the connected brace 2 and guard brace 22 is the distinctive diamond shape aperture 7. There are two points of connectivity or uninterrupted expanses of metal that conjoin the guard brace 22 to the brace 2. These connective points originate at the extreme inferior lateral region of the matrix 1. Preferably, located laterally and medially between these connective aspects are four wedge shaped cutouts or folding notches 28abcd. These are present on both connective aspects. The wedges 28abcd, are located at the horizontal midline of the brace 2 and the guard brace 22 (a horizontal line can be drawn to connect all four folding notches 28abcd). This permits for precise correlation when the brace 2 and guard brace 22 are folded or articulated (FIGS. 1B and 1C).

Positioned off center within the body of the guard brace 22 is an opening, aperture, or guard window 24. This window's 24 position is mirrored to that of the brace extrusion window 4. This allows both windows 4, 24 to align when the guard brace 22 is articulated with the brace 2 (folded along the notches 28abcd FIGS. 1B, 1C). When folded or articulated at the folding notches 28abcd, the result is a boomerang-shaped two layered band 1 having conjoined windows 25 that form a single aperture, which will be covered by a cover or flash guard 14, described below. The guard window 24 is also identical in size and dimension to the extrusion window 4. This identical sizing and correlative placement assures the windows will align and not interrupt one another (border overlapping) when the matrix 1 is articulated. The identical window sizing and correlative placement also permits universal compatibility with any inter-proximal contact area (the band is reversible).

Positioned on the superior and inferior circumference of the guard brace window 24 are two wedge-shaped notches 8b,10b. These notches, 8b10b are identical in size and mirror the placement to the brace extrusion window's 4 notches 8a,10a. The guard brace 22 superior window notch 8b is of a size and length as to permit viewing above the occlusal surfaces of two abutting teeth when the matrix band 1 is placed inter-proximally between a prepped first tooth 42, and a second tooth 44. The guard brace 22 inferior window notch 10b resides directly below the superior window notch 8b and is obscured when placed inter-proximally. Positioned a short distance below the guard brace 22 inferior window notch 10b is a slightly larger notch or gingival notch 12b. This notch 12b is associated with the inferior border of the brace 2. All of the matrix band's 1 superior 8a,8b, inferior 10a,10b and gingival 12a,12b notches correlate with one another when the matrix 1 is fully articulated.

Attached to the superior border of the guard brace 22 (when the band is articulated) or directly below the guard window 24 (as seen in FIG. 1A) is a flat flexible semi-rectangular cover or flash guard 14. Preferably, the flash guard 14 is an appropriately shaped continuous aspect of the guard brace 22 that has been formed from the same single piece of material as the body portions. The flash guard 14 is attached to the guard brace 22 by a narrow strip, tab, or severance junction 30. This severance junction 30 is positioned off center from the mid-point of the guard window 24. Positioned centrally on the lateral and medial aspects of the severance junction 30 are two wedge shaped cutouts or folding notches 29a,b. The folding notches 29a,b demarcate the midpoint between the bodies of the flash guard 14 and guard brace 22 to allow the two to correlate. When folded the guard brace 22 is folded at folding notches 29a,b of tab 30, the flash guard 14 completely covers the guard window 24. The flash guard 14 is of a length as to not interfere with the inferior border of an articulated matrix (does not reach the bottom of the guard brace 22 border or brace 2 border of an articulated matrix 1). This eliminates potential for gingival invasion in instances of guard 14 migration or dislodgement. The flash guard 14 width ensures adequate coverage of the lateral aspects of both apertures 24,4. Preferably, flash guard 14 is also formed from the same piece of material as the body portions. Although not economical, the flash guard 14 could be connected to the body by conventional means such as gluing or crimping. Also, although not economical, the flash guard 14 could be a completely separate piece of material inserted across the aperture.

Figure 22:
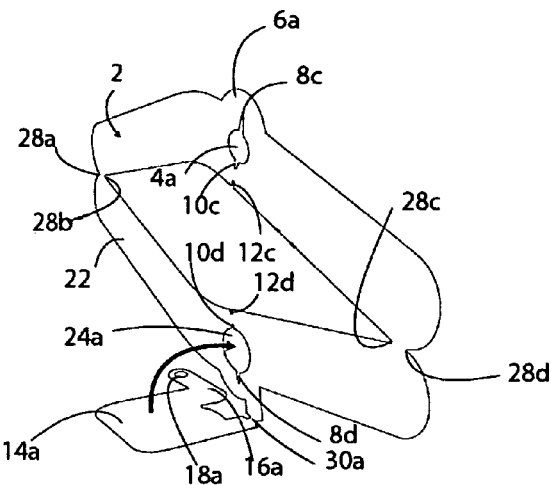
FIG. 22 shows the folding of the flash guard against the guard brace.
Figure 23:
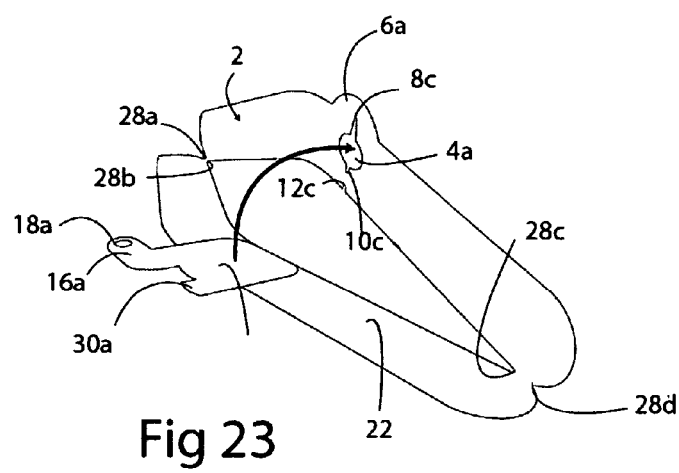
FIG. 23 shows the folded flash guard and guard brace being folded against the remaining matrix to form an articulated matrix.

Located on the superior border of the flash guard 14 (when folded, FIGS. 1B and 1C) is an "L" shaped peninsular extended portion, extension, flap, or guard removal tab 16. The removal tab is a continuous extension of the flash guard 14. When an articulated matrix 1 is placed inter-proximally, the removal tab 16 and connective severance junction 30 are visible above the bridge 6, FIG. 22. The position of the removal tab 16 and severance juncture 30 are offset as to permit (if physically cutting the juncture 30 is not desired) a rotational removal of the flash guard 14 from between the articulated matrix 1. The removal tab's 16 L shape directs the tab 16 away from the severance juncture's 30 location. This shape and deliberate direction enables a rotational removal by increasing the leverage. Additionally, the tab's 16 extension facilitates grasping with a hemostat or cotton pliers. Preferably, positioned within the extremities of the removal tab 16 is an ovoid hole or removal aperture 18 that is not in alignment with any part of guard window 24. This aperture is sized to be engaged by a suitable instrument for pulling the flash guard 14 away from the matrix band at the appropriate time.

FIG. 1B (Front View of matrix/flash guard articulation) depicts a guard brace 22 view of an articulated matrix band 1. The guard brace 22 is folded upward against the brace's 2 face. The central aspect of the flash guard's body 14 is visible through the opening of the guard window 24. Visible, above the matrix band 1 bridge 6, is the "L" shaped protrusion, or removal tab 16 and the folded protrusion that is the severance juncture 30. Located within the body of the removal tab 16 is a hole, opening, or removal aperture 18.

FIG. 1C (Rear View of matrix/flash guard articulation) depicts a matrix 1 side view of an articulated matrix 1. The central aspect of the flash guard 14 is visible through the opening of the brace extrusion window 4. Visible above the matrix band 2 bridge 6 is the "L" shaped removal tab 18 and the folded severance juncture 30. Visible within the confines of the visible removal tab 16 is a hole, opening, or removal aperture 18.

All of the notches described above are part of the preferred embodiment of the invention, as they either facilitate folding of the components of the matrix band or removal of the components of the matrix band from the tooth or both folding and removal. Such notches are not necessary to the operation of the invention.

ALTERNATIVE EMBODIMENTS—FIGS. 2-21

Figure 2A:
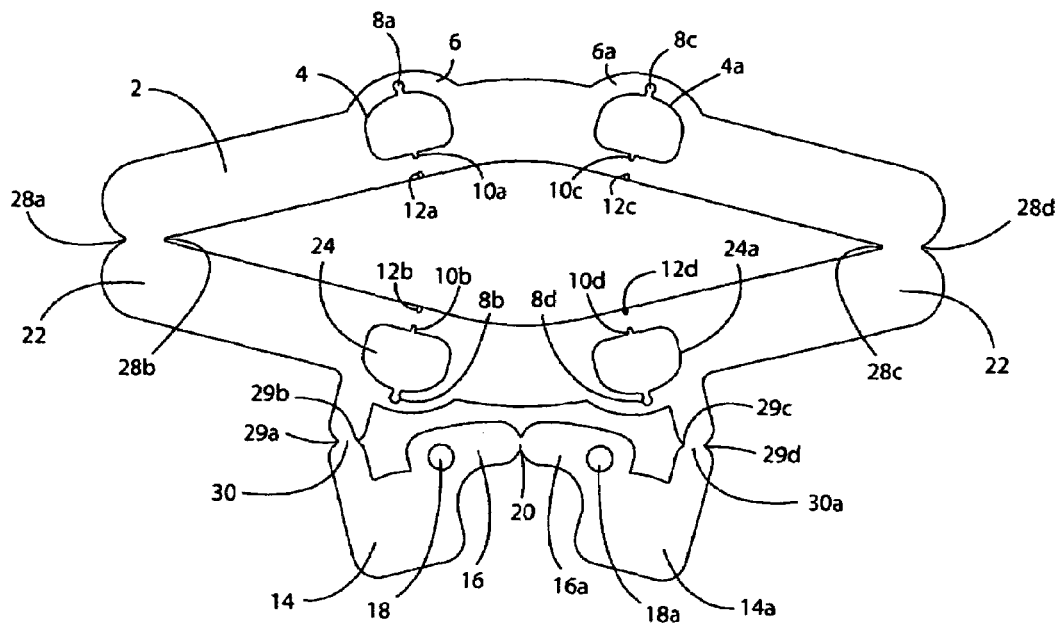
FIGS. 2A to 2C shows one unarticulated and two articulated views a medial, occlusal, distal ("MOD") or bilateral surface matrix with four apertures, mirrored guard brace and two flash guards with conjoined removal tabs.
Figure 2B:
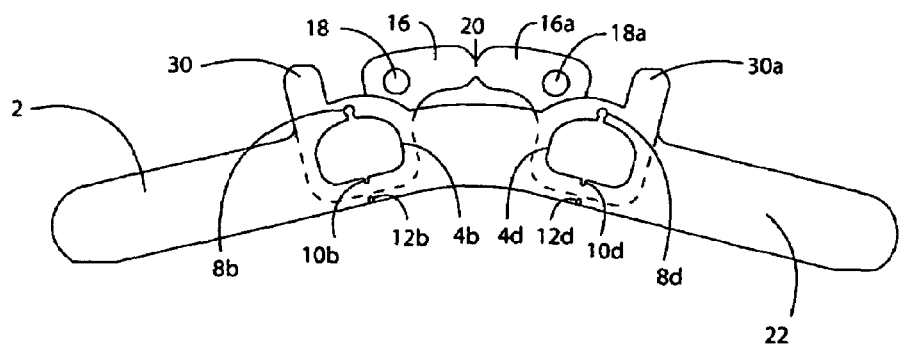
Figure 2C:
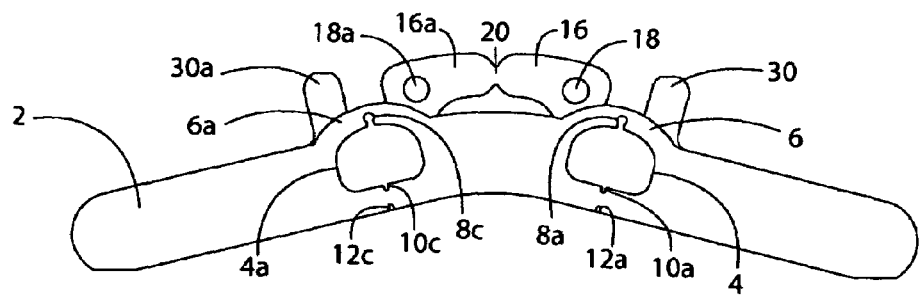

There are a multitude of possibilities for the barrier free matrix band with flash guard. These variations are all configured to best achieve optimal restorative versatility and secure matrix band 1, and flash guards 14,14a articulation. FIGS. 2A to 2C show various views of a MOD or bilateral matrix band 1. This matrix 1 laterally mirrors the extrusion window 4, guard window 24, bridge 6 flash guard 14, and severance juncture 30 of the preferred embodiment FIGS. 1A to 1C. This bilateral duplication of the above elements is positioned within the body of the matrix 1 to correlate with one or two prepared inter-proximal surfaces of a tooth. Both brace extrusion 4,4a and guard brace windows 4a, 24a are sized and spaced within the matrix 1 body to sufficiently accommodate the various dimensions of posterior teeth (bicuspid or molar) and allow for the range of patient tooth size variation, and contact point locations.

The double flash guard 14,14a configuration has a connection or tab juncture 20 joining each guard's 14,14a removal tab 16,16a. This juncture 20 creates a continuous connection, physically joining both flash guards 14,14a at the vertical midline of the matrix 1 body. To permit proper folding articulation (without distortion), both flash guards 14,14a have an oblique connective orientation with regard to the severance junctures 30,30a. This oblique angle is slanted medially, toward the matrix 1 vertical midline, with both flash guards 14,14a directed or slightly tilted toward one another. The flash guards 14,14a to severance junctures 30,30a, relationships creates a linear folding axis by horizontally aligning the associated folding notches and foldable region of the junctures 30,30a (A straight line can be drawn through folding region of both severance junctions 30,30a). A horizontal folding axis allows for a vertical, simultaneous articulation of both guards 14,14a with the matrix 1 body.

The shape and positioning of the removal tabs 16,16a and tab junction 20 forms an opening or void of metal upon articulation. This void is visible between the inferior border of the tabs 16,16a, tab junction 20 and the superior border of the matrix body 1 (FIGS. 2B and 2C). This void is sufficiently sized to allow a cutting device such as a scissors or dental hand piece and burr to sever the tab junction 20 region and permit independent flash guard 14,14a withdrawals. While intact, (prior to severance) the conjoined tabs 16,16a exhibit and promote cooperative flash guard 14,14a flexion when the articulated matrix is placed into a retaining device. Present in both flash guards 14,14a removal tabs 16,16a are flash guard 14,14a removal apertures 18,18a. These apertures 18,18a are laterally offset from the connective tab junctures 20. This off center placement minimizes the chance of inadvertent cutting of the removal apertures 18,18a when severing the tab juncture 20.

Figure 3A:
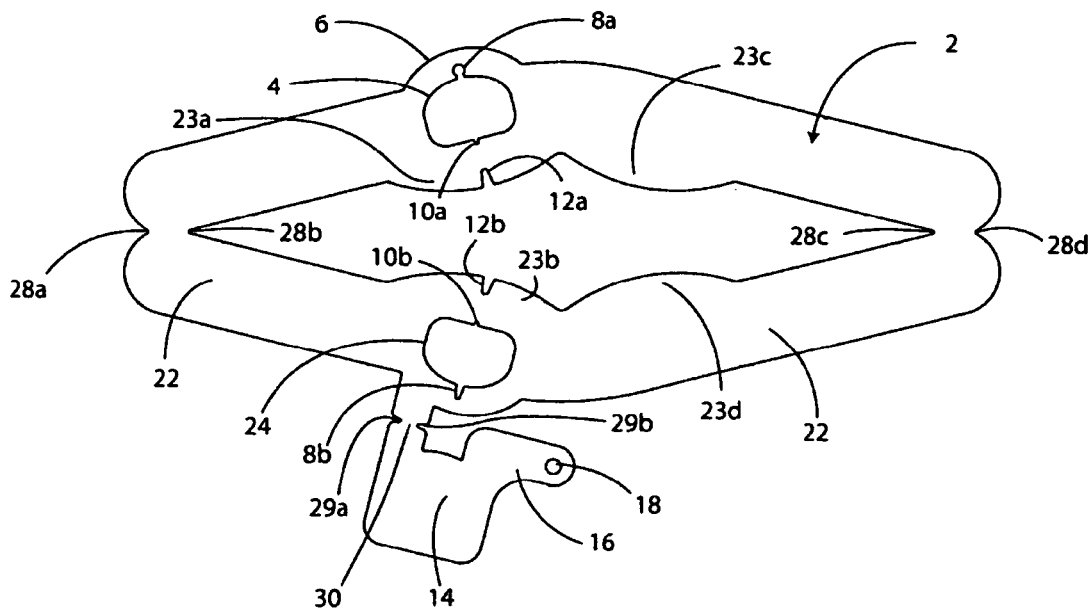
FIGS. 3A to 3C shows one unarticulated and two articulated views of a deep prep or molar medial occlusal/medial distal ("MO/DO") matrix with extended expanses of metal positioned beneath the apertures.
Figure 3B:
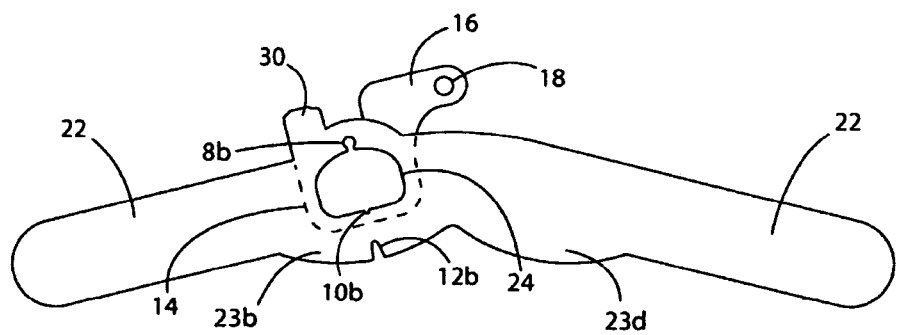
Figure 3C:
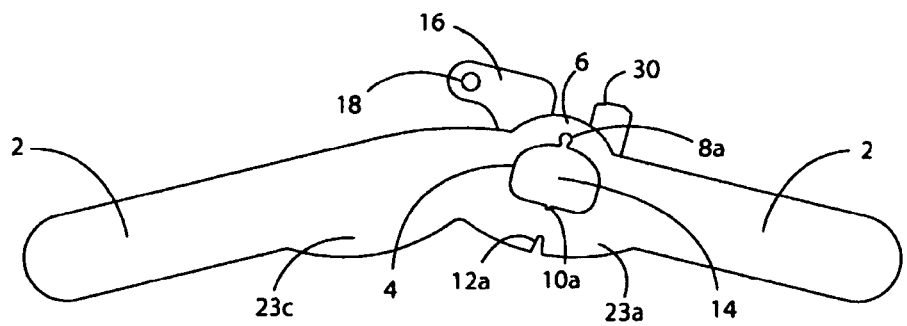
Figure 4A:
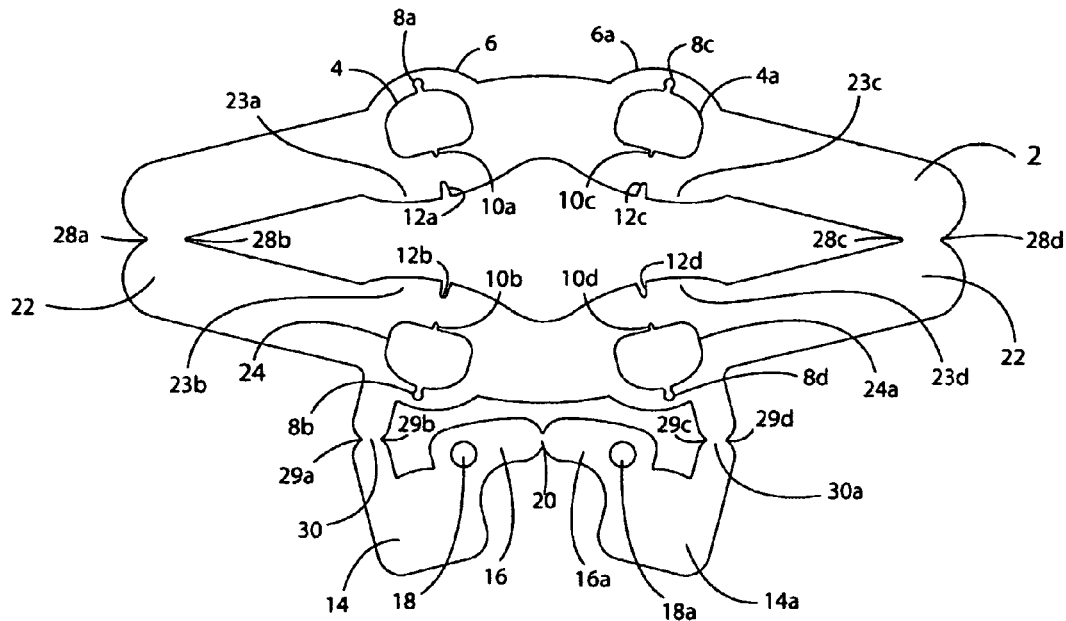
FIGS. 4A to 4C shows one unarticulated and two articulated views of a molar MOD matrix with extended expanses of metal positioned beneath all four apertures.
Figure 4B:
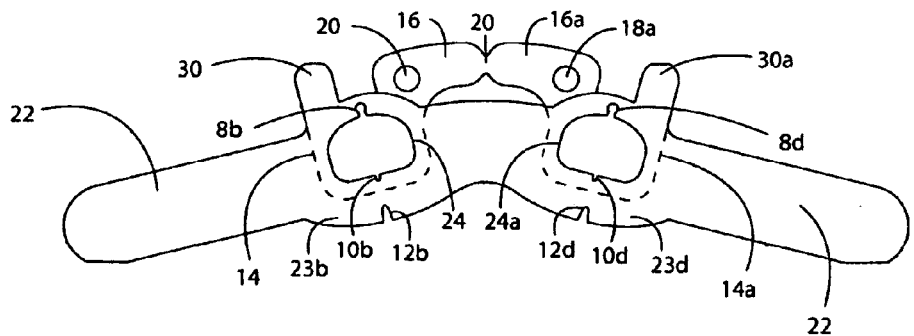
Figure 4C:
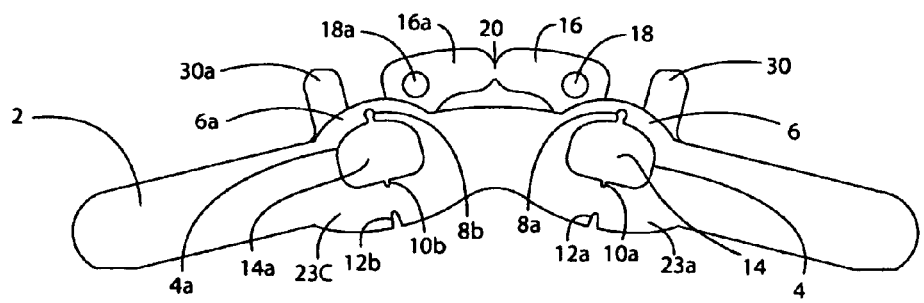

FIGS. 3A to 3C show various views of a deep prep or molar MO/DO matrix 1 with one brace extrusion window 4 and flash guard 14. Located beneath the brace extrusion 4 and guard brace extrusion 24 windows are gingival extensions 23a,b,c,d (semi-elliptical appendages or scallop-shaped expanses of metal). These extensions 23a,b,c,d (similar in size and shape to conventional Tofflemire-like deep prep matrices) are positioned directly below the brace extrusion window 4 and guard brace extrusion window 24 to accommodate sub-gingival molar preparations. FIGS. 4A to 4C show various views of a deep prep MOD matrix band with two brace extrusion windows 4,4a, a guard brace 22 that mirrors the shape and position of the brace 2, two guard brace extrusion windows 24,24a, and a two connected flash guards 14,14a. Positioned beneath each of the four windows are gingival extensions 23a,b,c,d (semi-elliptical appendages or scallop shaped expanses of metal). These extensions 23a,b,c,d (similar in size and shape to conventional Tofflemire-like deep prep matrices) are positioned directly below both brace extrusion 4,4a, and guard brace 24,24a extrusion windows to accommodate sub-gingival molar preparations.

Figure 5A:
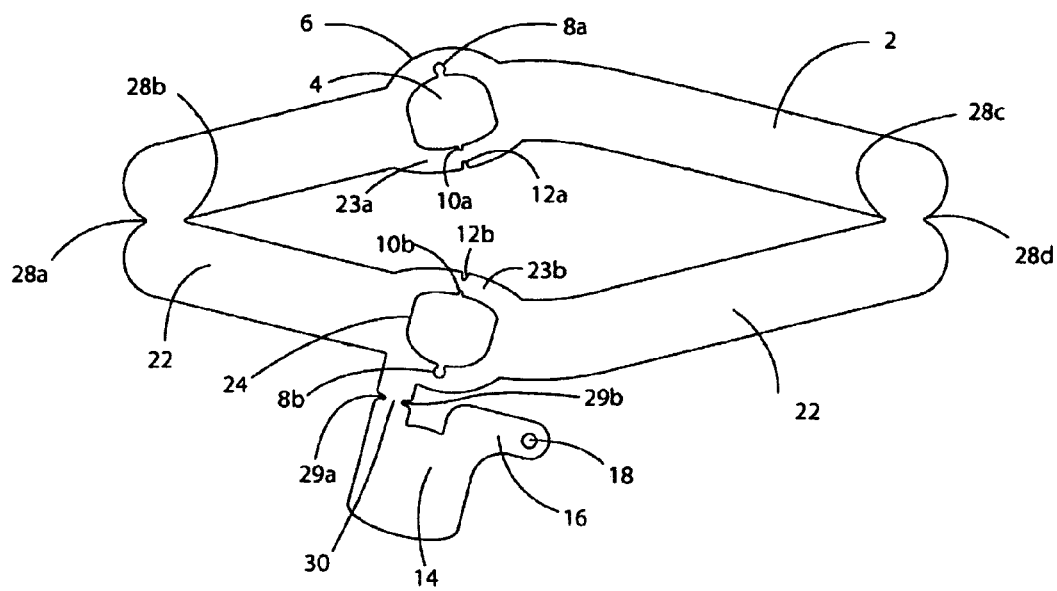
FIGS. 5A to 5C shows one unarticulated and two articulated views of a deep preparation MO/DO matrix with two inferiorly elongated apertures.
Figure 5B:
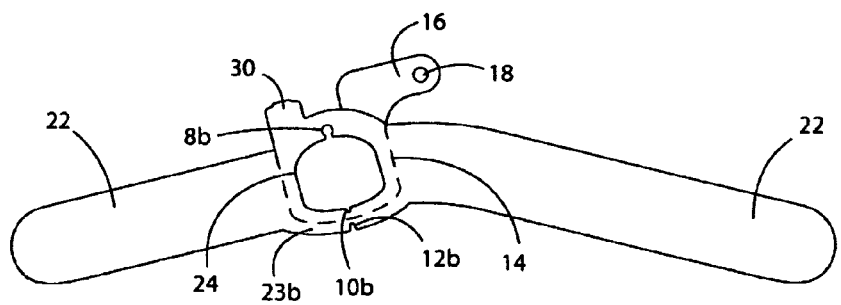
Figure 5C:
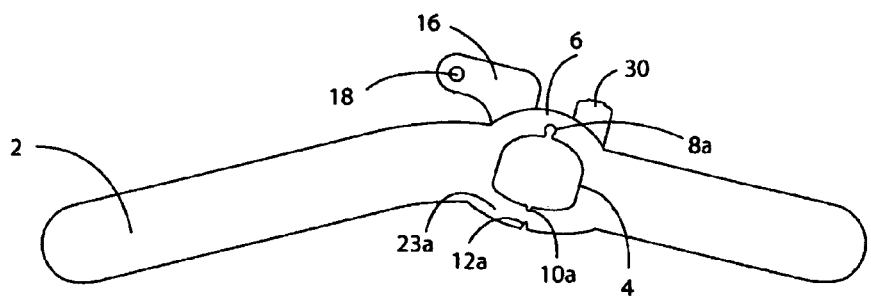
Figure 6A:
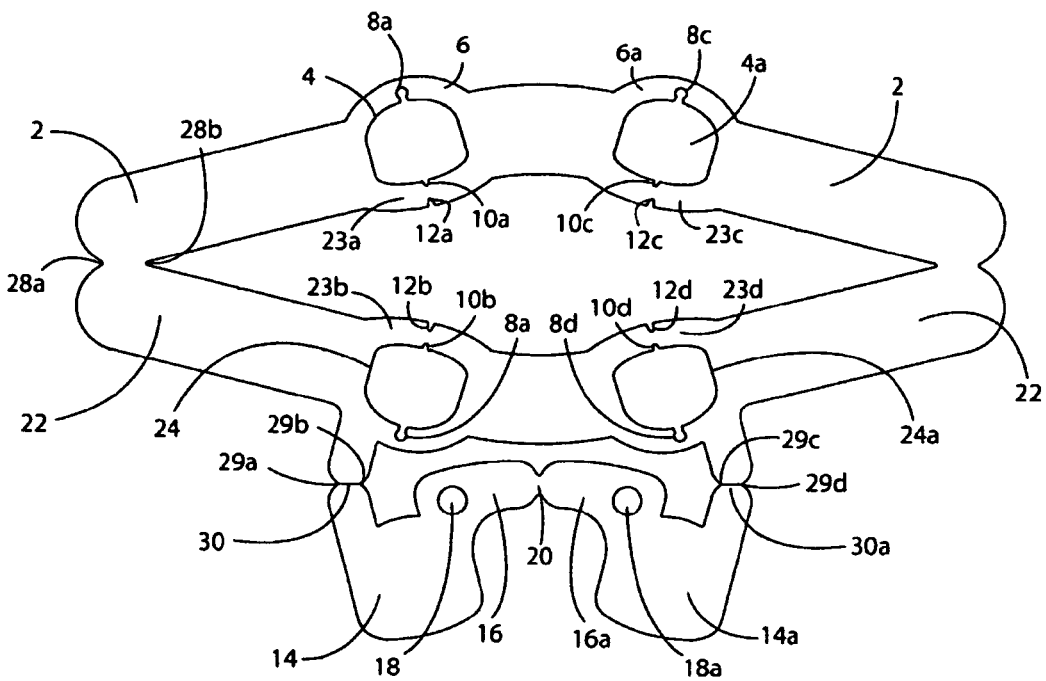
FIGS. 6A to 6C shows one unarticulated and two articulated views of a deep preparation MOD matrix with four inferiorly elongated apertures.
Figure 6B:
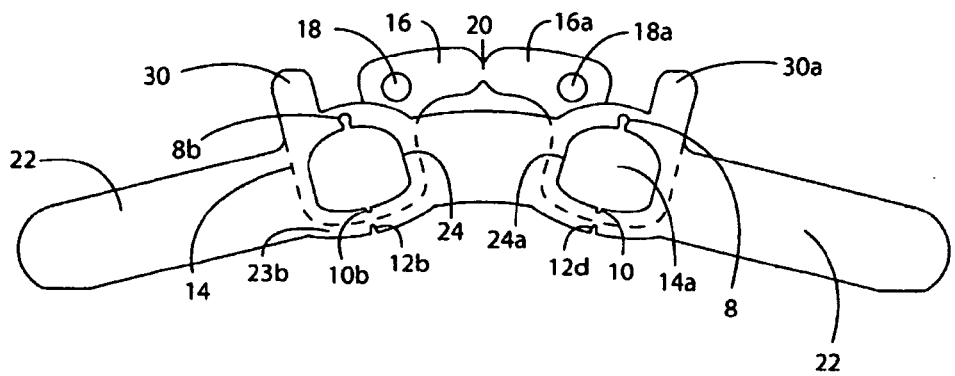
Figure 6C:
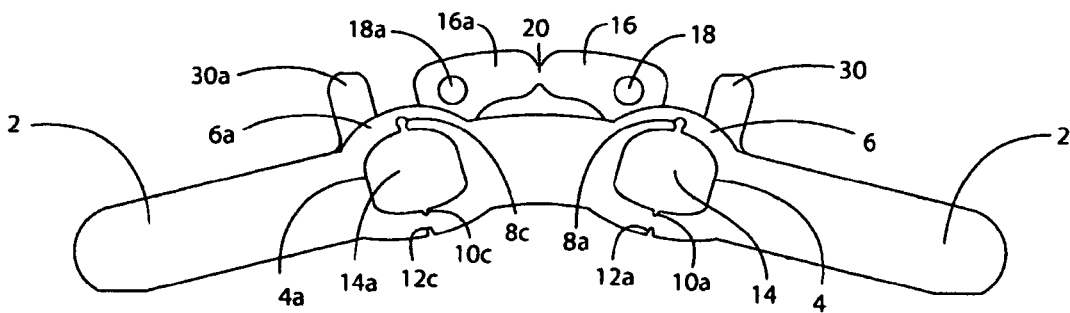

FIGS. 5A to 5C show various views of a MO/DO matrix 1 with one brace extrusion window 4, a guard brace 22 that mirrors the shape and position of the brace 2 and a flash guard 14. The inferior aspects of both the brace extrusion window 4 and guard brace window 24 are elongated for deep preparations. The inferior matrix 1 border below the windows is bulged or convexly extended to accommodate the added length of the brace extrusion 4 and guard brace 24 windows. FIGS. 6A to 6C show various views of an MOD matrix with two brace extrusion windows 4,4a, a guard brace 22 that mirrors the shape and position of the brace 2, two guard brace extrusion windows 24,24a and two connected flash guards 14,14a. The inferior aspects of both the brace extrusion windows 4,4a and guard brace extrusion windows 24,24a are elongated for deep preparations. The inferior edge of the matrix 1, below each extended window, is convexly bulged to accommodate the added length.

Figure 7A:
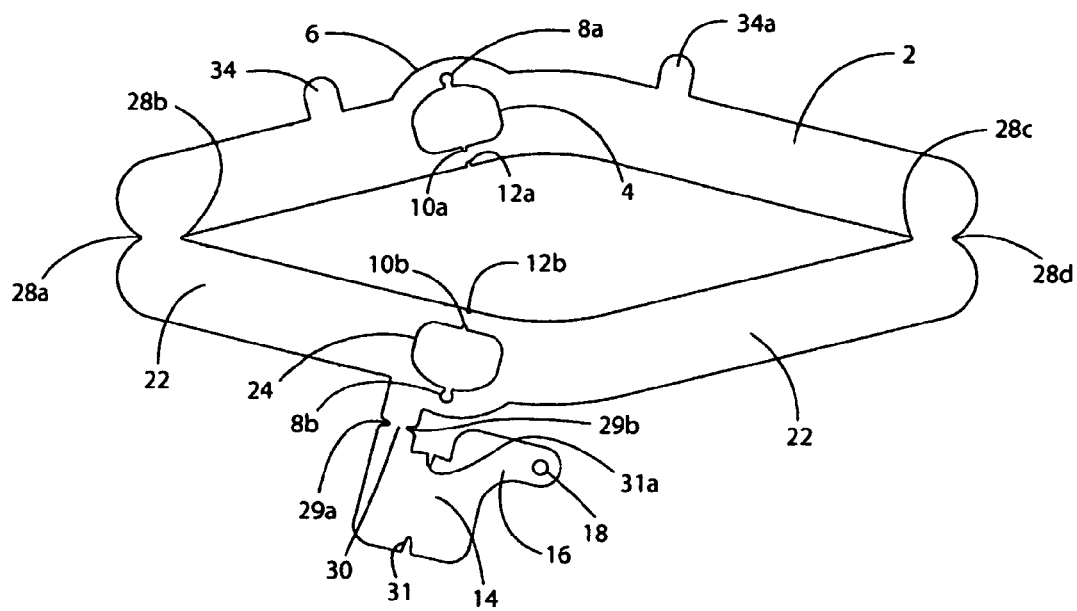
FIGS. 7A to 7C shows one unarticulated and two articulated views of a MO/DO matrix with foldable securing tabs and notched flash guard.
Figure 7B:
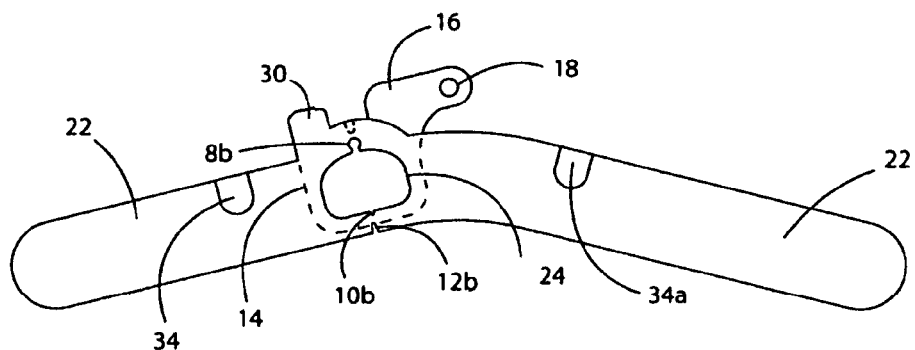
Figure 7C:
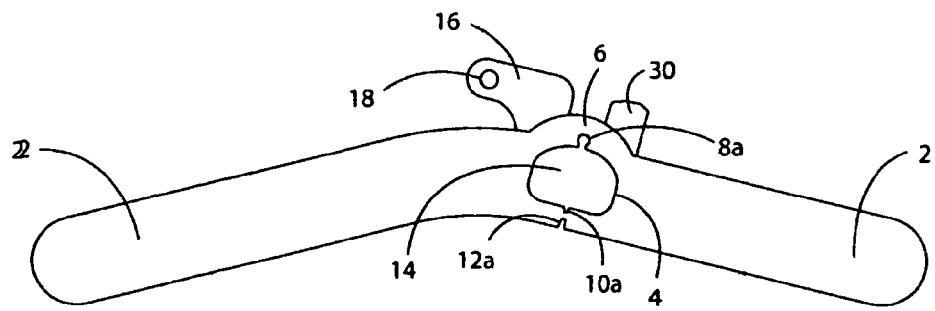
Figure 8A:
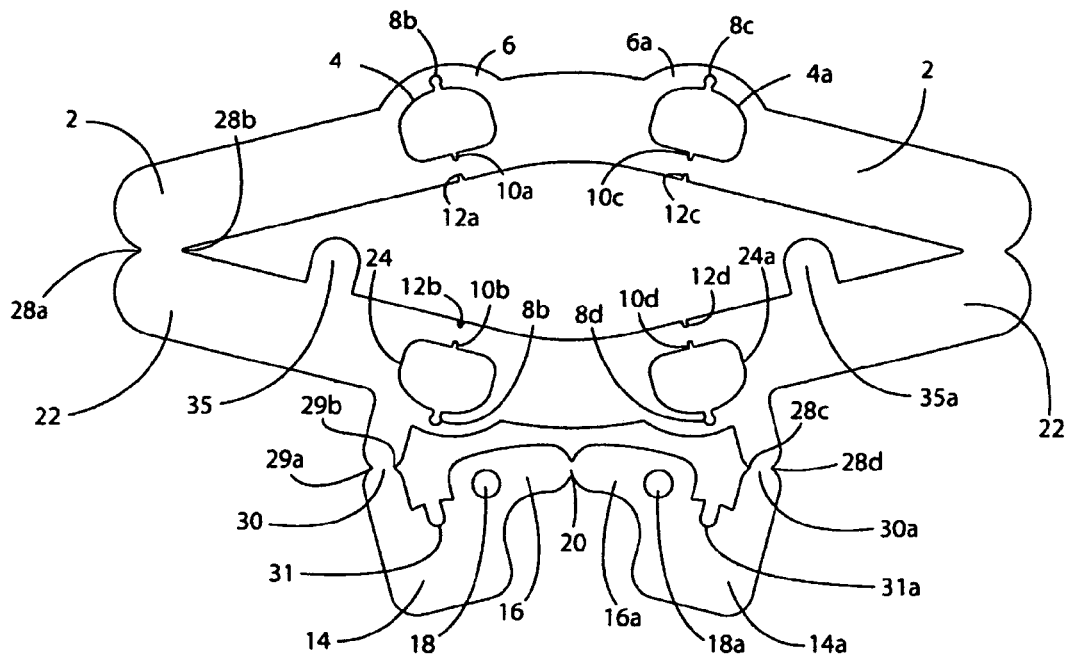
FIGS. 8A to 8C shows one unarticulated and two articulated views of a MOD matrix with inferiorly positioned securing extensions and a two notched conjoined flash guards.
Figure 8B:
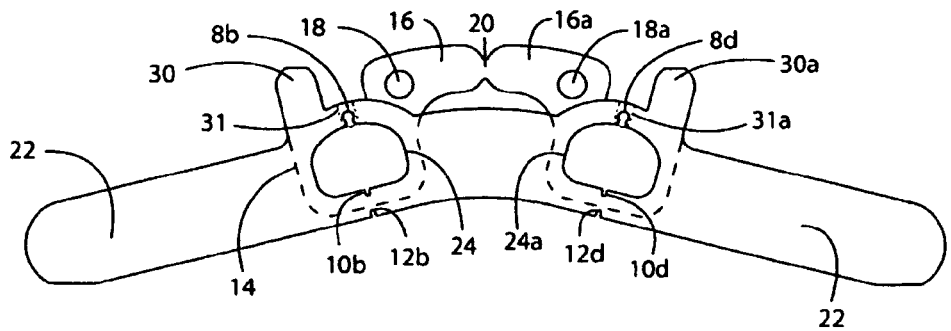
Figure 8C:
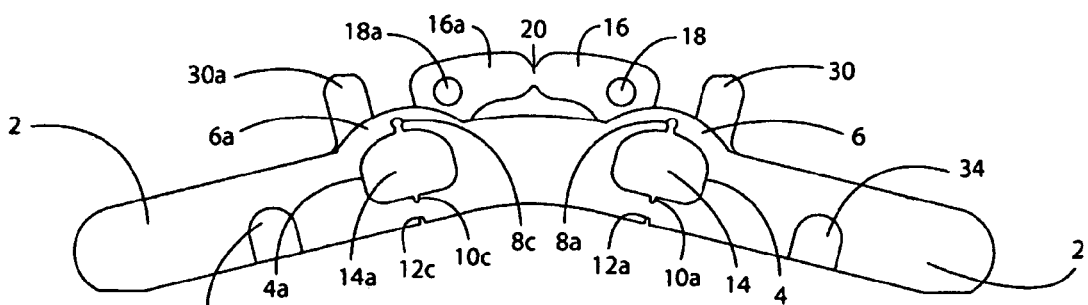

FIGS. 7A to 7C show various views of a MO/DO matrix with one brace extrusion window 4, a mirrored guard brace 22, a guard brace extrusion window 24 and a flash guard 14. Located on the superior border of the brace 2 are two tab-like protrusions or buccal lingual extensions, 34,34a. After matrix 1 articulation, the extensions 34,34a are configured to fold downward against the guard brace 22, mechanically locking them together. Incorporated into the superior and inferior aspects of the flash guard 14 are "V" shaped cutouts or folding notches 31, 31a. These notches 31, 31a are oriented to facilitate maximal flash guard 14 flexion when the matrix 1 is flexed circumferentially and placed into a matrix retainer 40. FIGS. 8A to 8C show various views of a MOD brace 2 with two brace extrusion windows 4,4a, a mirrored guard brace 22, two guard brace extrusion windows 24,24a, two connected flash guards 14,14a. Located on the inferior border of the guard brace 22 are two tab-like protrusions or buccal lingual extensions 35,35a. After articulation, the extensions 35,35a fold upward against the brace 2 (FIG. 8A), mechanically locking both band aspects together. Incorporated into the superior aspect of the flash guards 14a,b (When the matrix 1 is articulated) are "U" shaped folding notches 31a,b. These notches 31,31a, are sized and positioned to permit for both flexibility and visibility through the superior window notches 8abcd of the aligned brace extrusion window 4,4a and guard extrusion window 24,24a (when the matrix 1 is articulated FIGS. 8B and 8C).

Figure 9A:
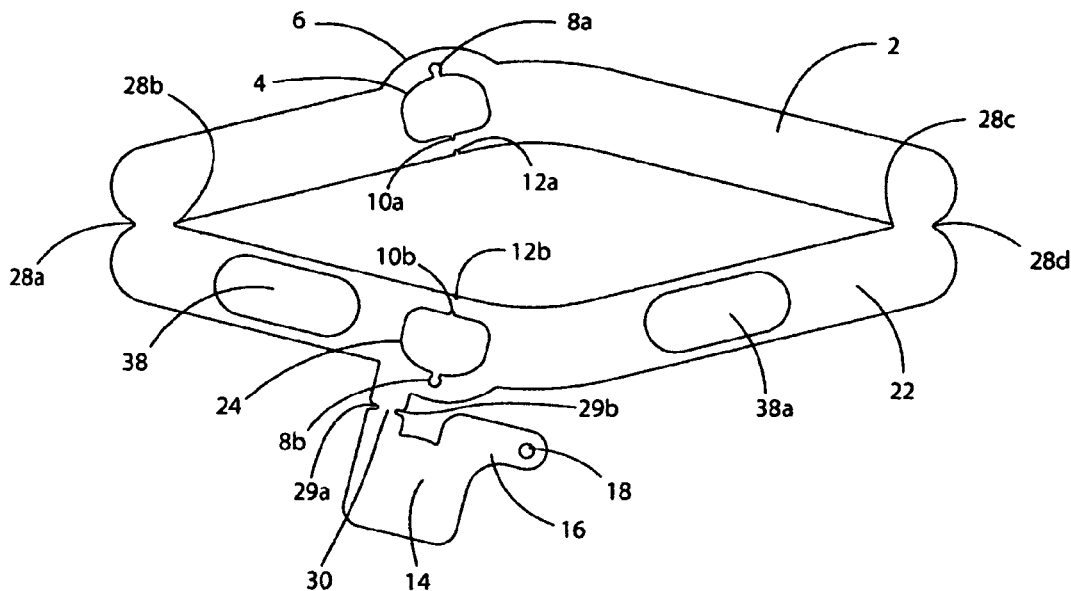
FIGS. 9A to 9C shows one unarticulated and two articulated views of a MO/DO matrix with an applied adhesive application on two separate regions of the matrix band.
Figure 9B:
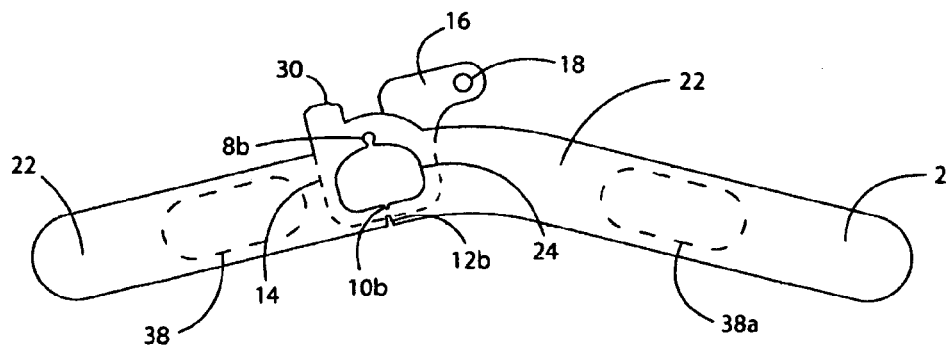
Figure 9C:
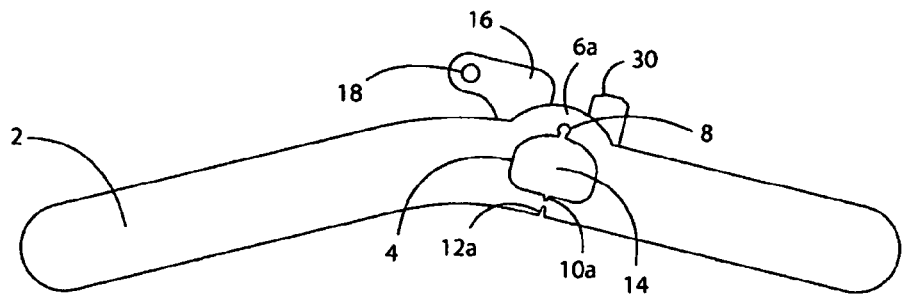
Figure 10A:
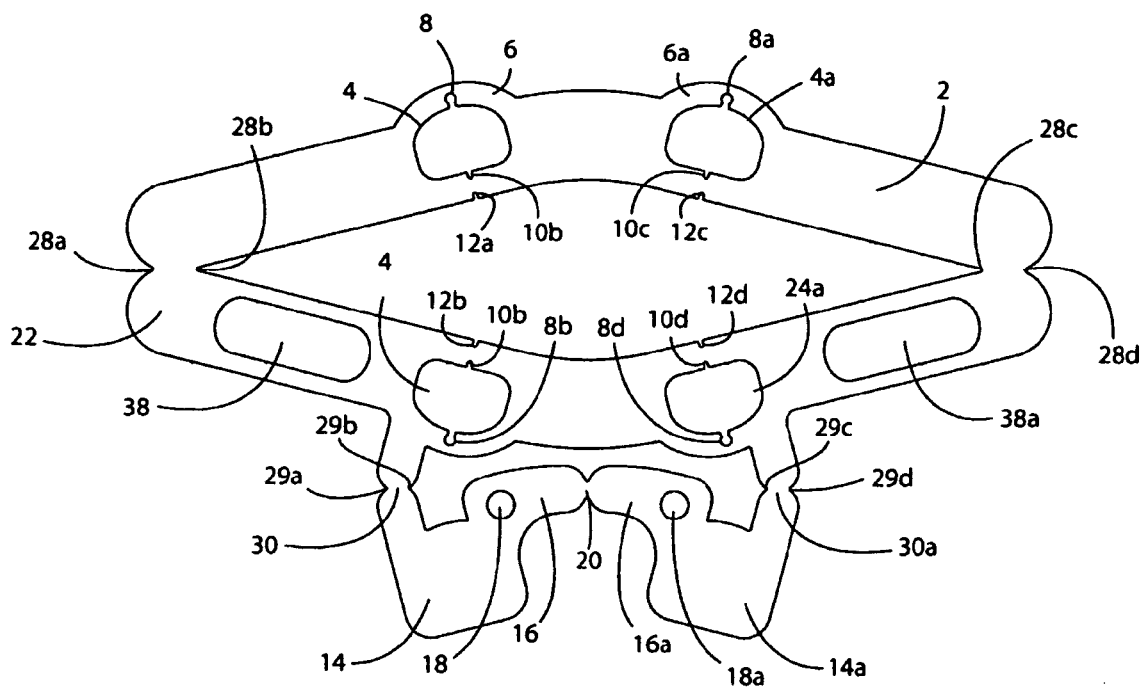
FIGS. 10A to 10C shows one unarticulated and two articulated views of a MOD matrix with an applied adhesive application on two separate regions of the matrix band.
Figure 10B:
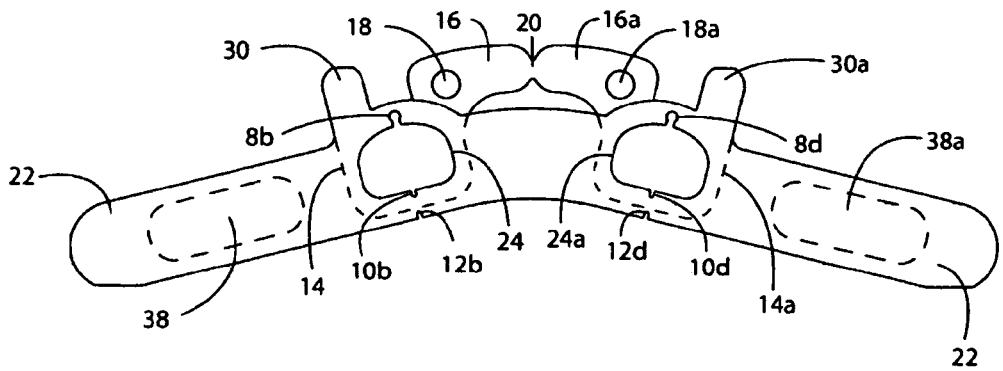
Figure 10C:
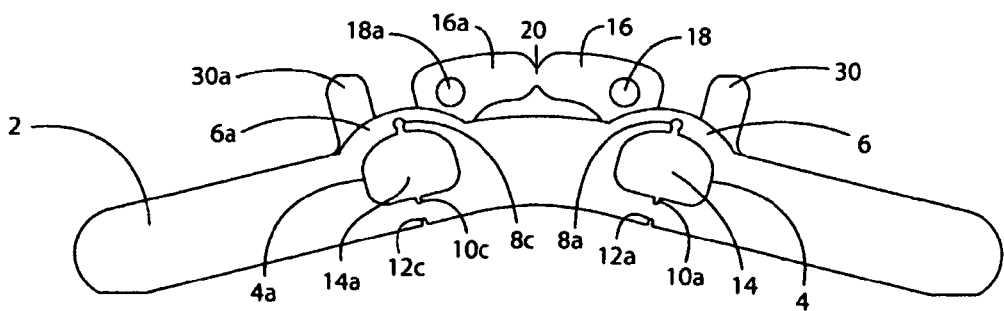

FIGS. 9A to 9C show various views of a MO/DO brace 2 with one extrusion window 4, a mirrored guard brace 22, one guard brace extrusion window 24 and a flash guard 14. Applied to the body of the guard brace 22 is an adhesive application 38,38a that secures the matrix 1 upon folding articulation. The positioning of the adhesive strip 38,38a is beyond the operative region of the flash guard 14, brace extrusion window 4 and guard brace extrusion window 24. This prevents any adhesive related complications during operative employment. FIGS. 10A to 10C show various views of a MOD brace 2 with two brace extrusion windows 4,4a, a guard brace 22 that mirrors the shape and position of the brace 2, two guard brace extrusion windows 24,24a, and two connected flash guards 14,14a. Applied to the body of the guard brace 22 are adhesive applications 38,38a that secures the matrix upon articulation. The positioning of the adhesive strips 38 are beyond the functional regions of the flash guards 14,14a, brace extrusion windows 4,4a and guard brace extrusion windows 24,24a. This prevents any adhesive related complication during operative employment.

Figure 11A:
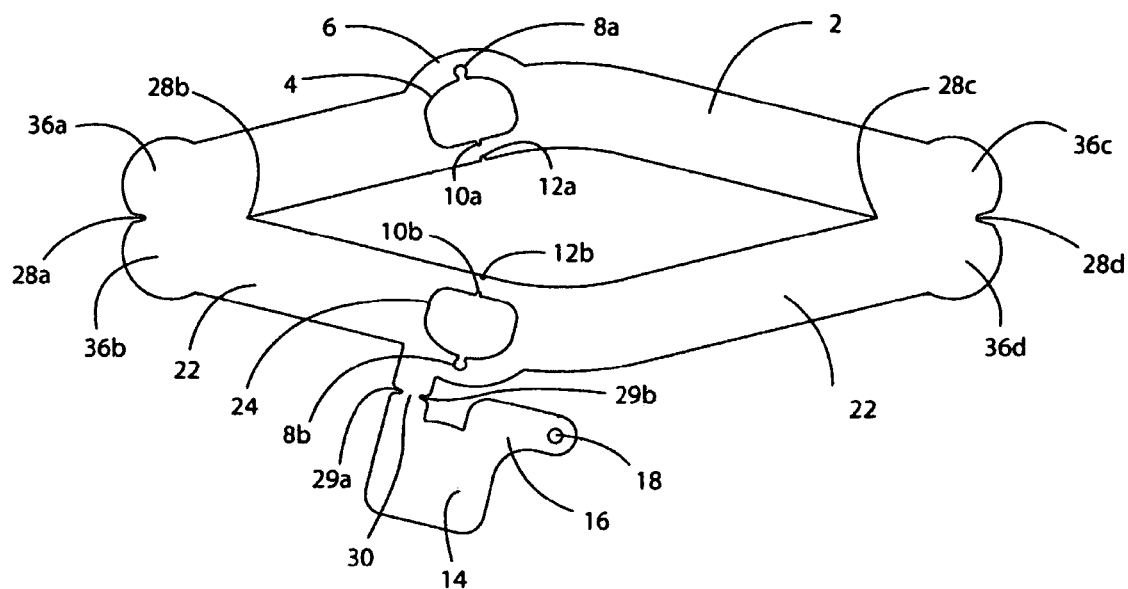
FIGS. 11A to 11C shows one unarticulated and two articulated views of a MO/DO vertically compressed space saving matrix design having compensating retainer grip extensions.
Figure 11B:
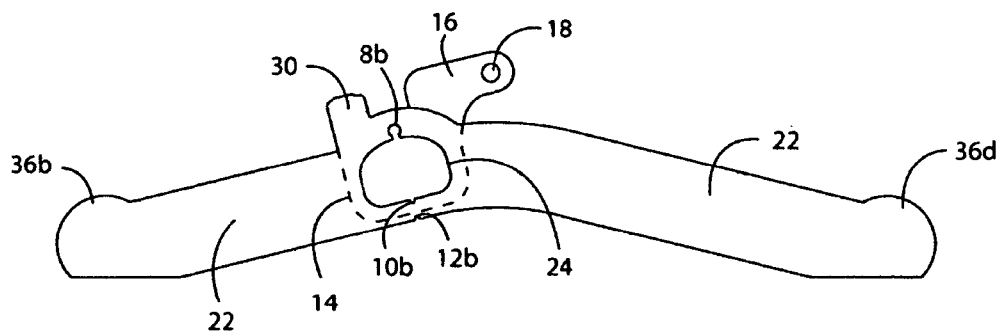
Figure 11C:
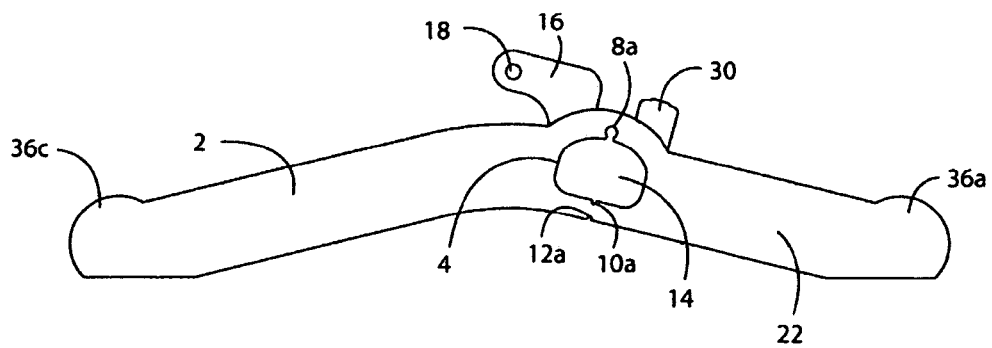
Figure 12A:
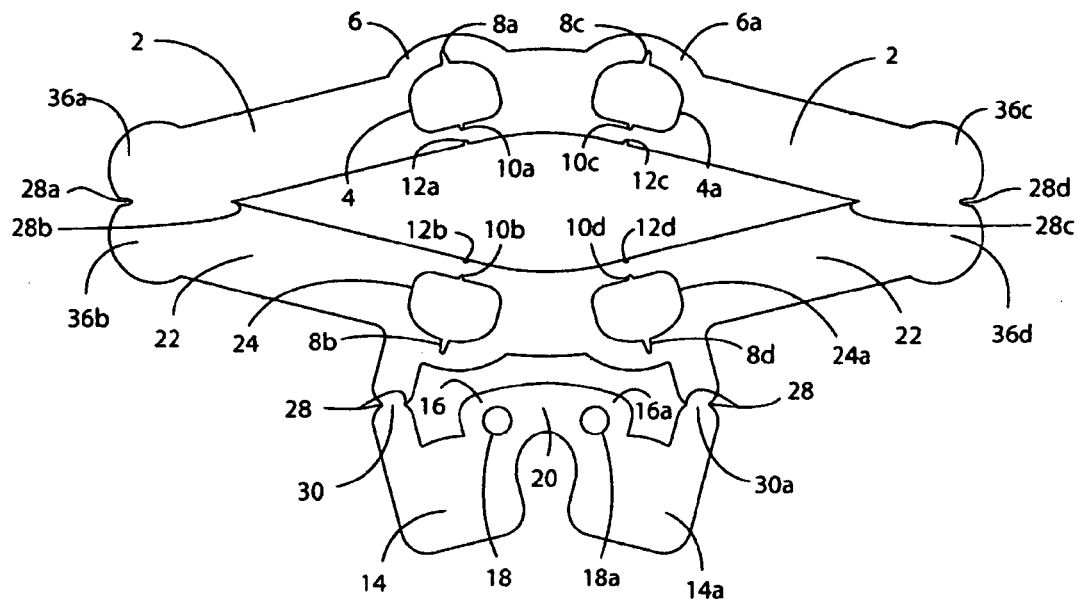
FIGS. 12A to 12C shows one unarticulated and two articulated views of a MOD vertically compressed space saving matrix design having compensating retainer grip extensions.
Figure 12B:
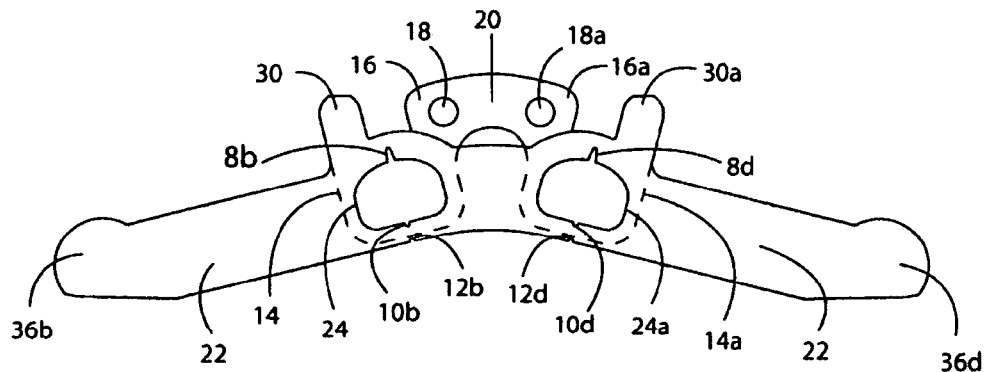
Figure 12C:
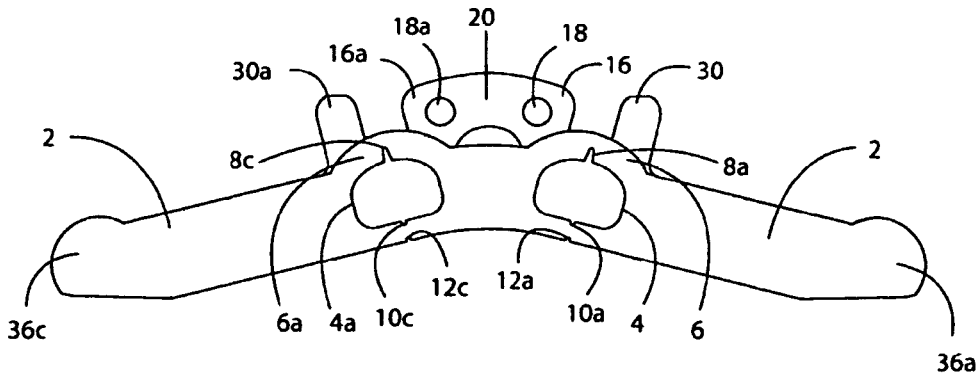

FIGS. 11A-11C show various views of a vertically compressed MO/DO matrix band 1, brace 2, having two extrusion apertures 4,24, a mirrored guard brace 22, a flash guard 14 and compensating retainer grip extensions 36a,b,c,d. The vertically compressed configuration is designed for teeth having reduced vertical dimensions. The bodies of the brace 2 and guard brace 22 are fused closer together. The retainer extensions 36a,b,c,d approximate the lost metal (resulting from a shortened total band height) to provide adequate area for a retaining device 40 to grip. FIGS. 12A-12C show various views of a vertically compressed MOD matrix band 1 having a brace 2 two brace extrusion windows 4,4a a mirrored guard brace 22, two guard brace extrusion windows 24,24a two connected flash guards 14,14a and compensating retainer grip extensions 36a,b,c,d. The vertically compressed configuration is designed for teeth having reduced vertical dimensions. The retainer extensions 36a,b,c,d approximate the lost metal to ensure a positive gripping area for the retaining device 40.

Figure 13A:
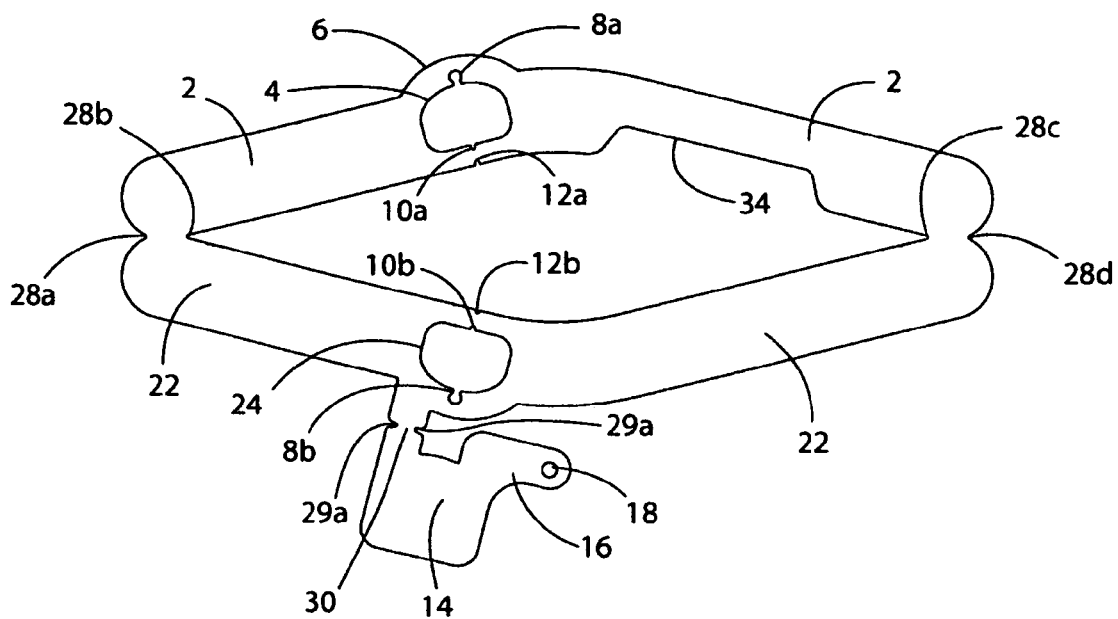
FIGS. 13A to 13C shows one unarticulated and two articulated views of a MO/DO matrix with an inferiorly contoured section of band on the aspect of the matrix opposed to the apertures to aid insertion.
Figure 13B:
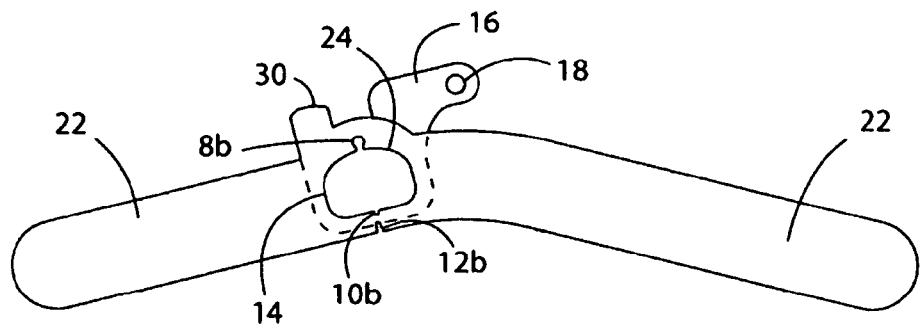
Figure 13C:
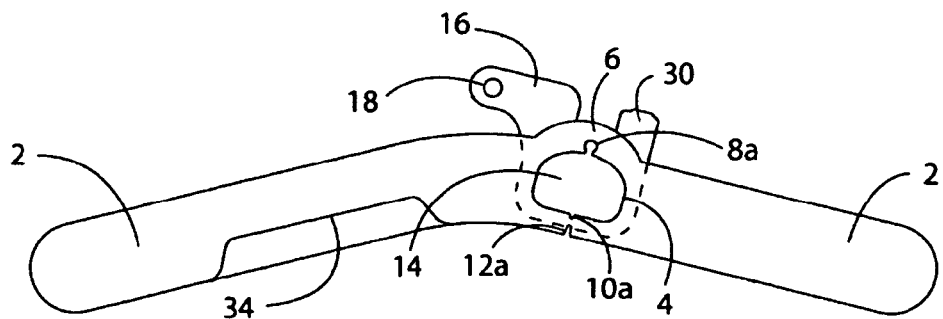

FIGS. 13A to 13C show various views of a MO/DO matrix 1, a brace 2 an extrusion window 4, a mirrored guard brace 22, guard window 24, and flash guard 14. Located on the body of the brace 2 opposite of the extrusion window 4 is a contoured metal section 41. The contoured region, located on the inferior brace 2 border, reduces the total band thickness (when articulated) that is inserted into an intact or unprepared inter-proximal contact space. This contour is of sufficient height and position as to not interfere with the initial insertion into an inter-proximal contact area.

Figure 14A:
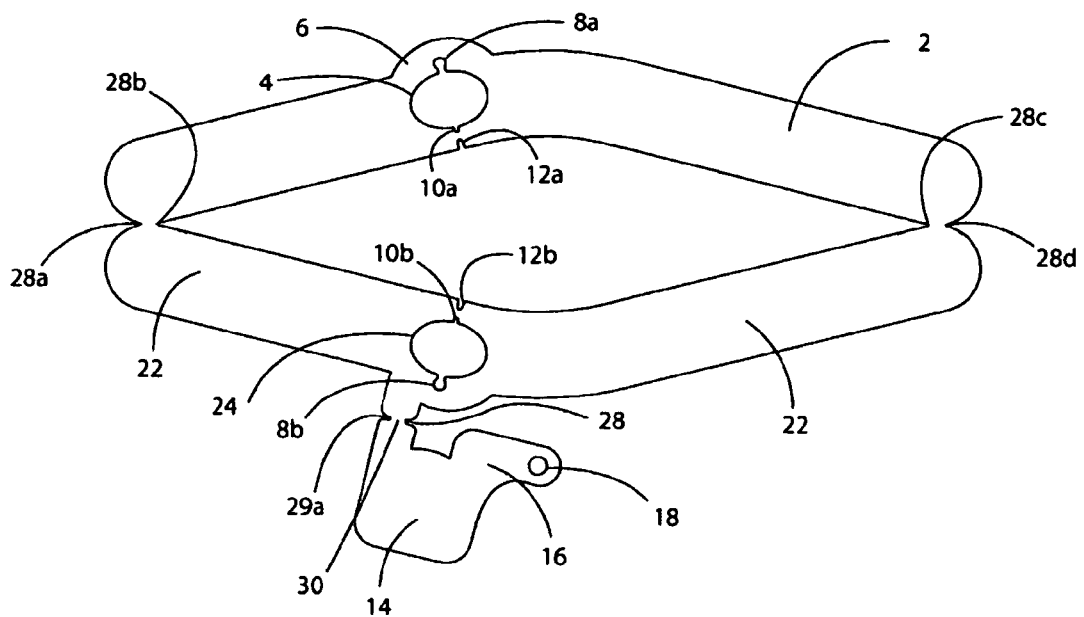
FIGS. 14A to 14C shows one unarticulated and two articulated views of a MO/DO matrix with ovoid apertures.
Figure 14B:
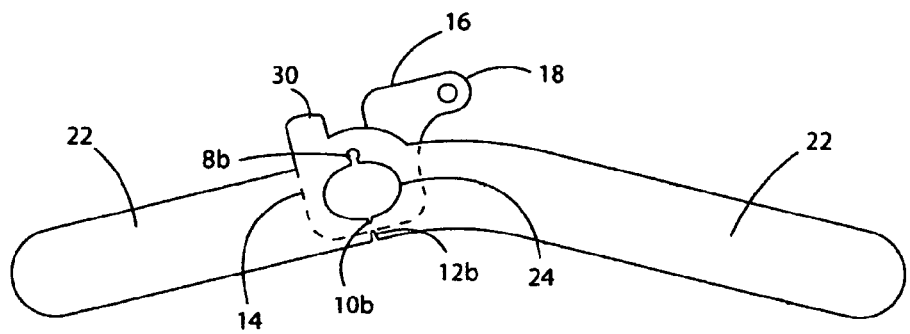
Figure 14C:
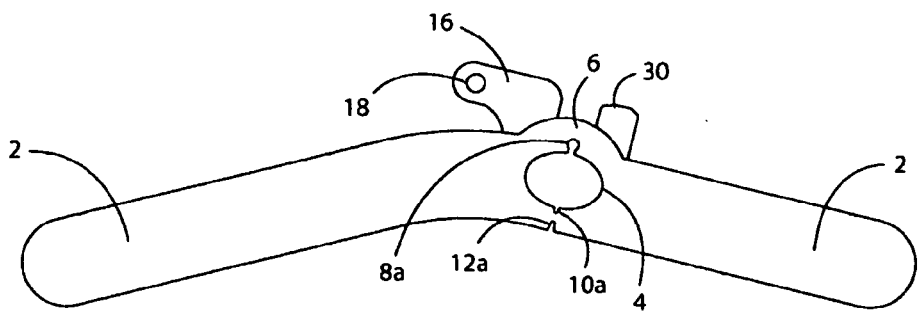
Figure 15A:
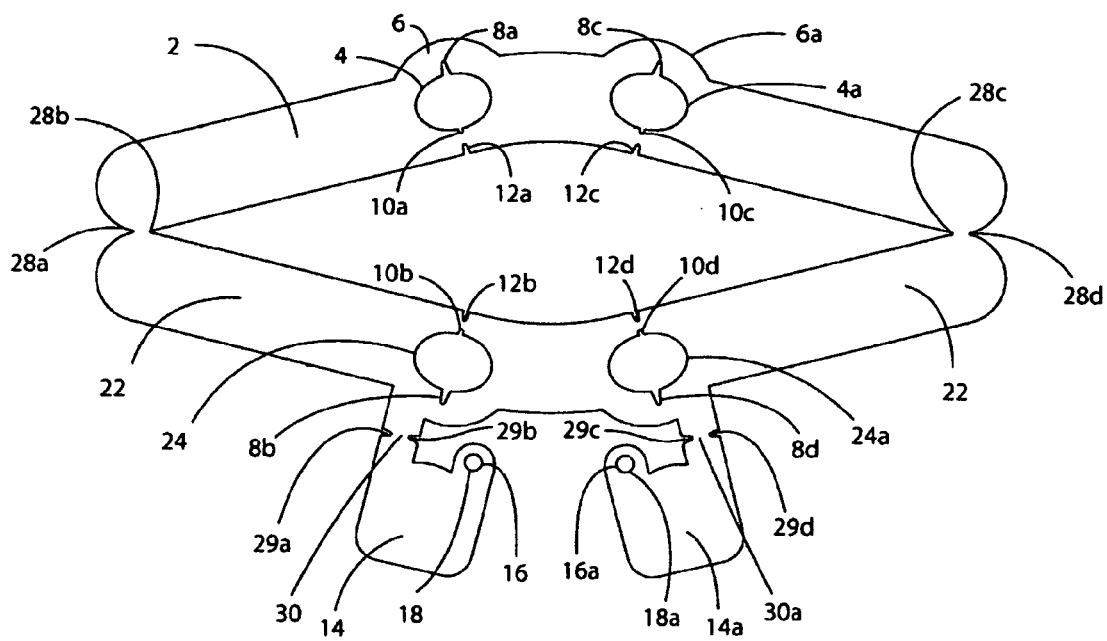
FIGS. 15A to 15C shows one unarticulated and two articulated views of an MOD matrix with equally sized ovoid windows and disconnected flash guard removal tabs.
Figure 15B:
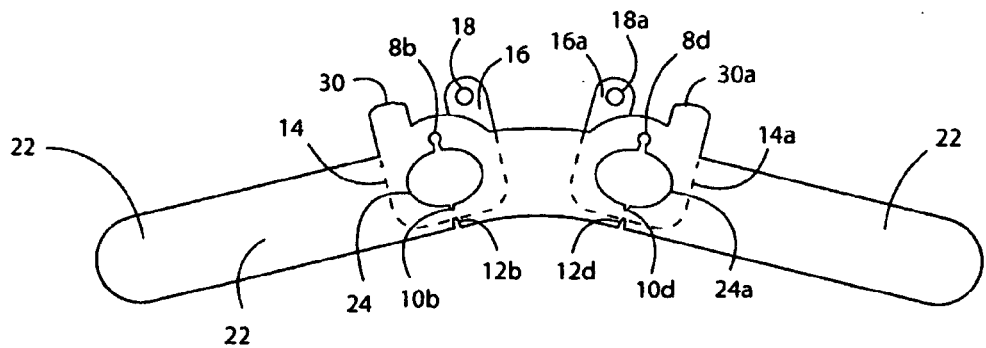
Figure 15C:
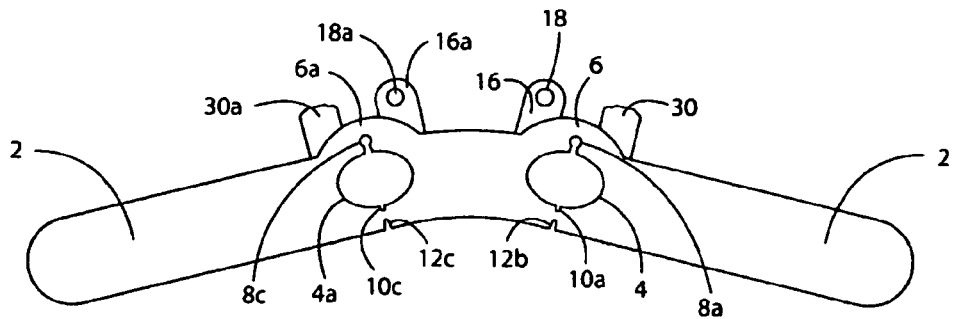
Figure 16A:
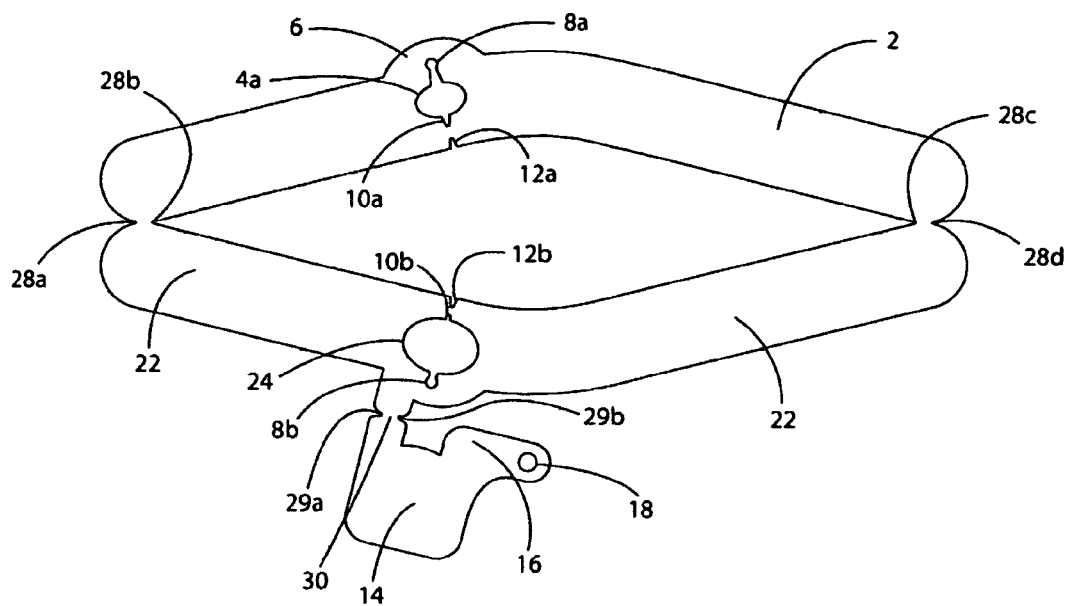
FIGS. 16A to 16C shows one unarticulated and two articulated views of a MO/DO matrix with offset sized ovoid apertures.
Figure 16B:
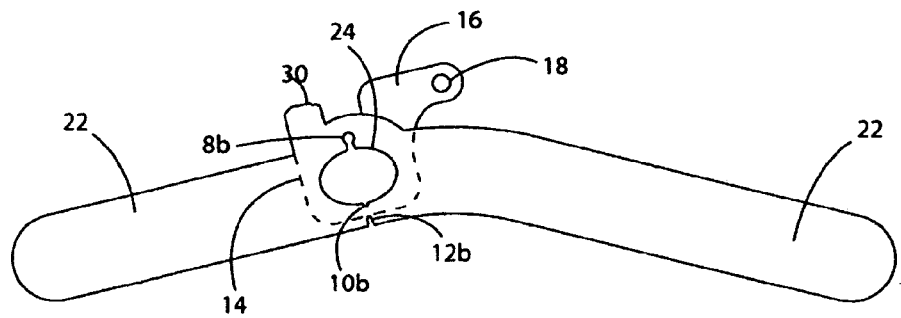
Figure 16C:
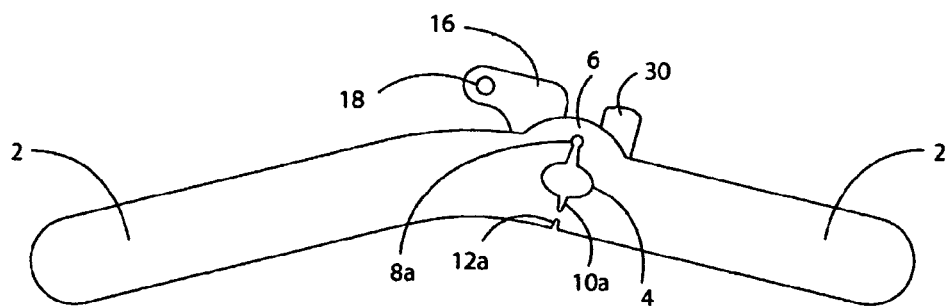
Figure 17A:
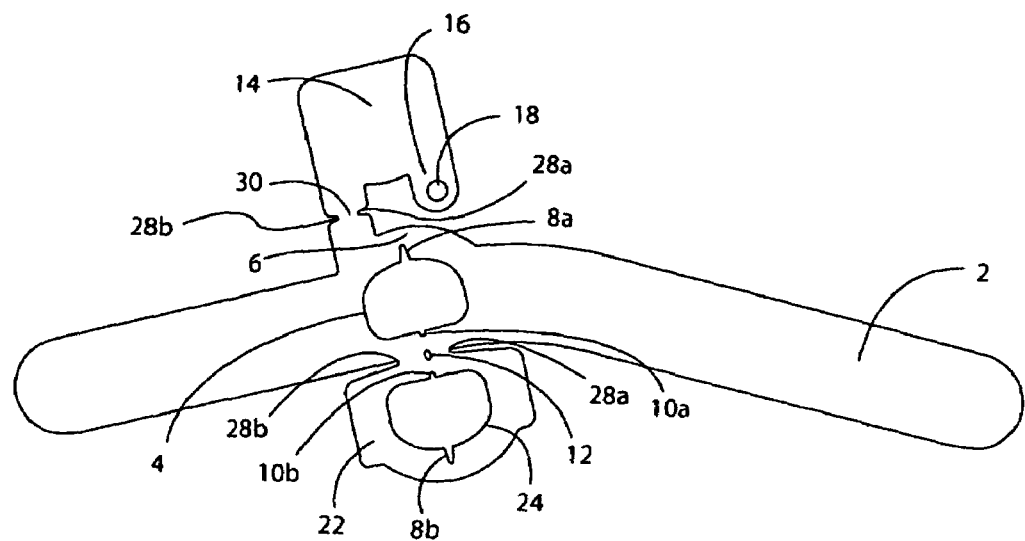
FIGS. 17A to 17C shows one unarticulated and two articulated views of a MO/DO matrix with a laterally shortened guard brace, guard brace aperture, and a superiorly connected flash guard.
Figure 17B:
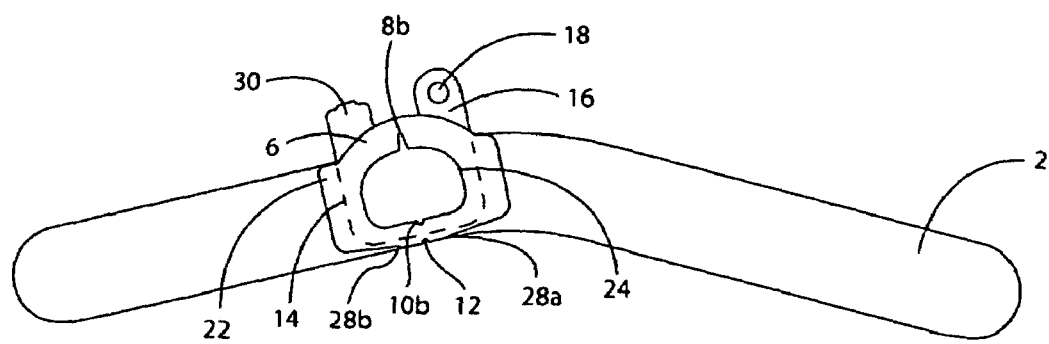
Figure 17C:
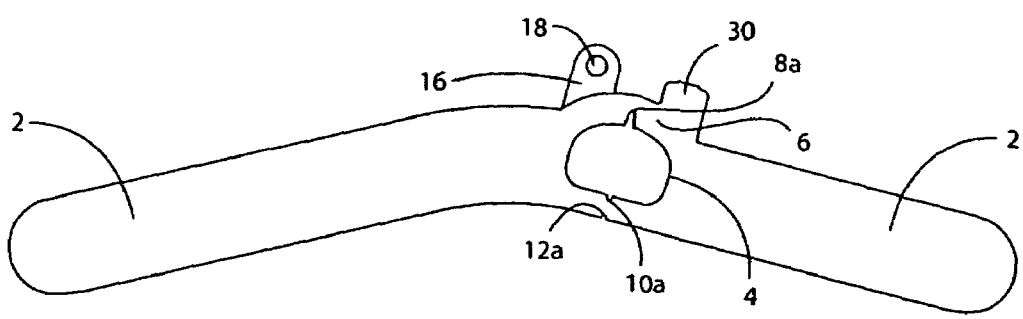

FIGS. 14A to 14C show various views of a MO/DO matrix band 1 with a brace 2, extrusion window 4, a mirrored guard brace 22, one guard brace extrusion window 24, and a flash guard 14. The brace extrusion window 4 and guard brace extrusion window 24 are elliptical in shape and identical in size. FIGS. 15A to 15C show various views of a MOD matrix 1 with a brace 2, two brace extrusion windows 4,4a, a mirrored guard brace 22, two guard windows 24,24a, and two disconnected flash guards 14,14a. The tabs 16,16a are not joined. The brace extrusion windows 4,4a and guard brace windows 24,24a are elliptical in shape and identical in size. FIGS. 16A to 16C show various views of a MO/DO matrix 1 with a brace 2, one brace extrusion window 4, a guard brace 22 that mirrors the shape and position of the brace 2, one guard brace extrusion window 24 and a flash guard 14. The brace extrusion window 4 and guard window 24 are elliptical in shape and offset in size.

Figure 18A:
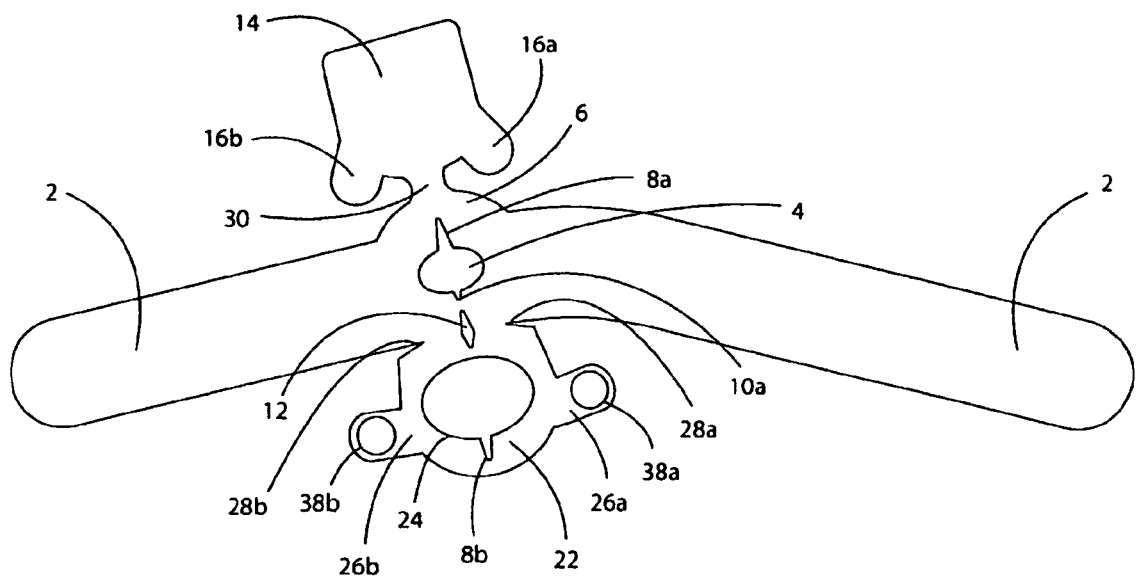
FIGS. 18A to 18C shows one unarticulated and two articulated views of a matrix with one aperture, a centrally connected flash guard, and two flash guard extensions.
Figure 18B:
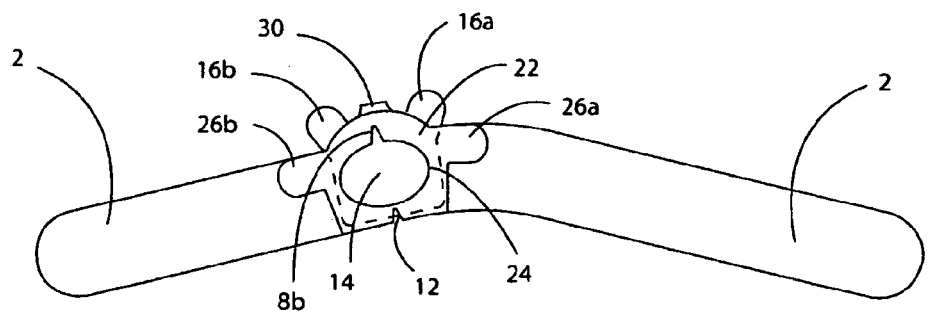
Figure 18C:
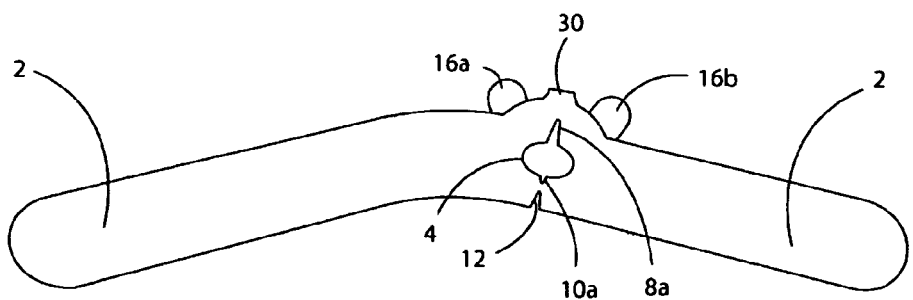

17A-17C shows a matrix 1 with brace 2, an attached flash guard 14, extrusion window 4, smaller guard brace 22 and guard brace extrusion window 24. The guard brace's 22 connective aspects reside directly below the brace extrusion window 4 on the brace 2. The body of the guard brace 22 is sufficient in height and width to accommodate the brace extrusion window 4. When the matrix 1 is articulated, the shortened brace 22 is positioned against the prep side of a tooth. FIGS. 18A to 18C shows a matrix 1, a brace 2 with a connected flash guard 14 extrusion window 4, smaller guard brace 22, and guard brace extrusion window 24. The flash guard 14 is positioned centrally above the brace extrusion window 4 and connected to the superior aspect of the bridge 6 by a severance junction 30. The flash guard 14 has two removal tabs 16a,16b. The guard brace 22 is positioned directly below the brace extrusion window 4 on the brace 2 and guard brace securing tabs 26a,26b with adhesive applications 38a,38b. The guard brace 22 aspect is placed against either side of a prepared surface.

Figure 19A:
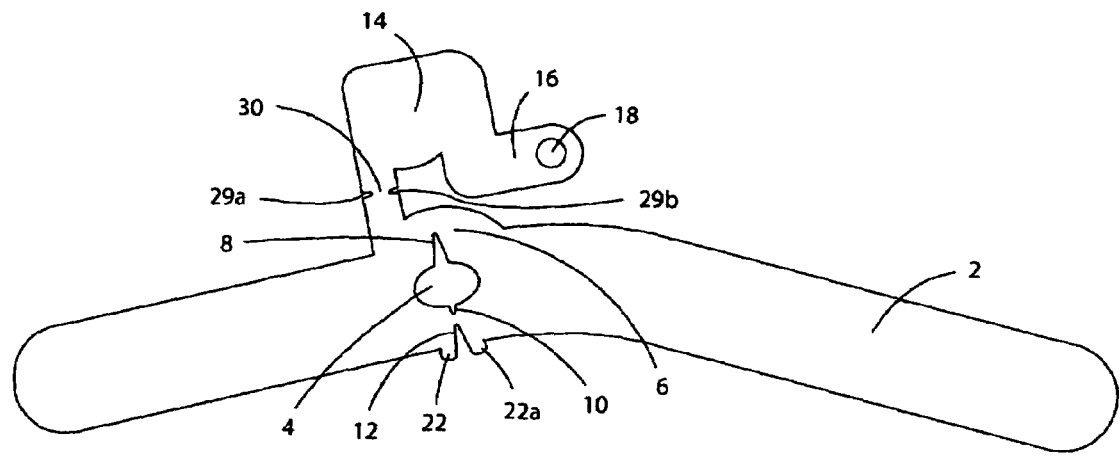
FIGS. 19A to 19C shows one unarticulated and two articulated views of a matrix with a connected flash guard and smaller wing-like guard braces.
Figure 19B:
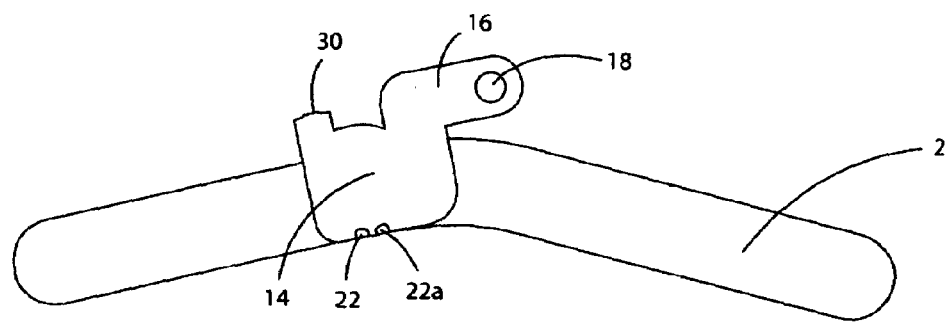
Figure 19C:
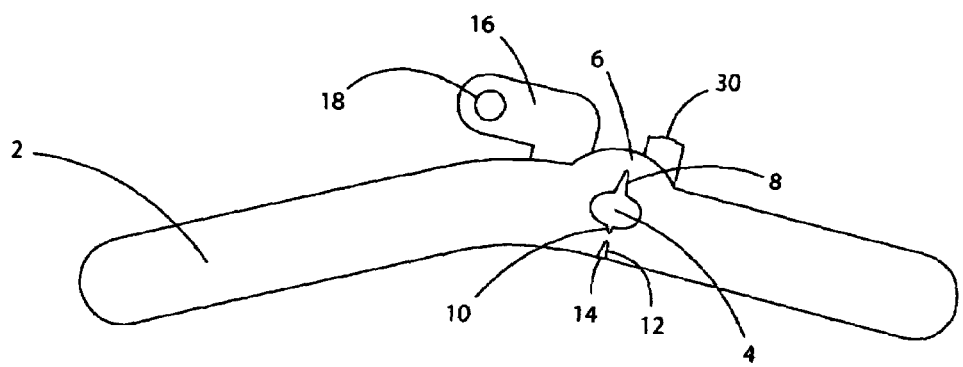
Figure 20A:
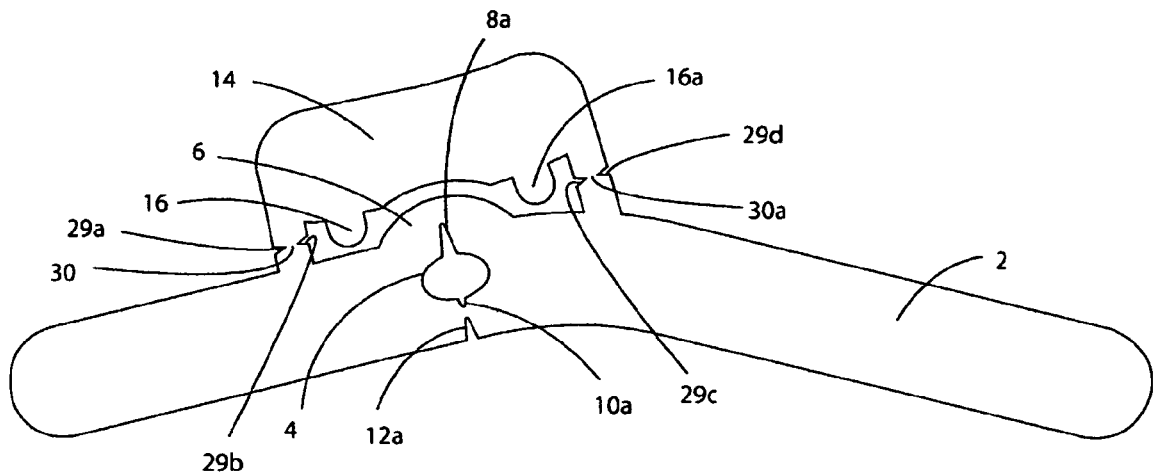
FIGS. 20A to 20C shows one unarticulated and two articulated views of a matrix with a double connected flash guard and two removal tabs.
Figure 20B:
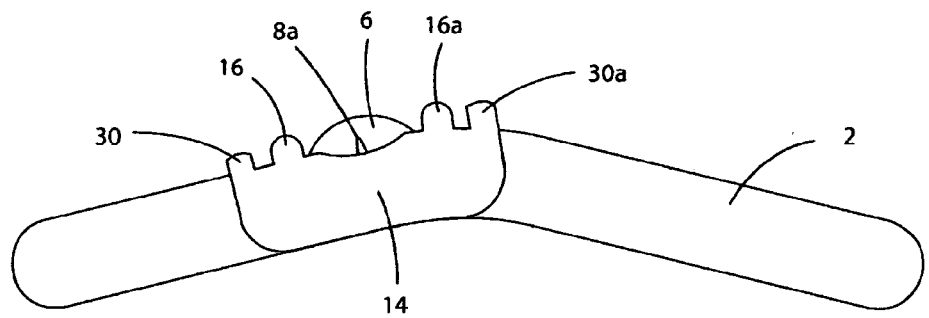
Figure 20C:
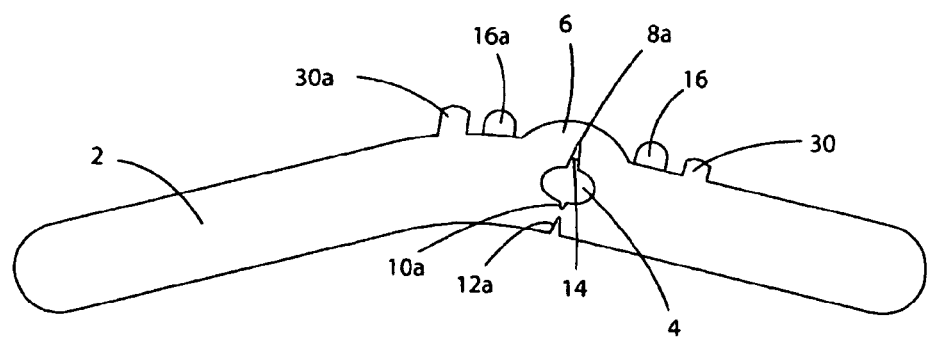
Figure 21A:
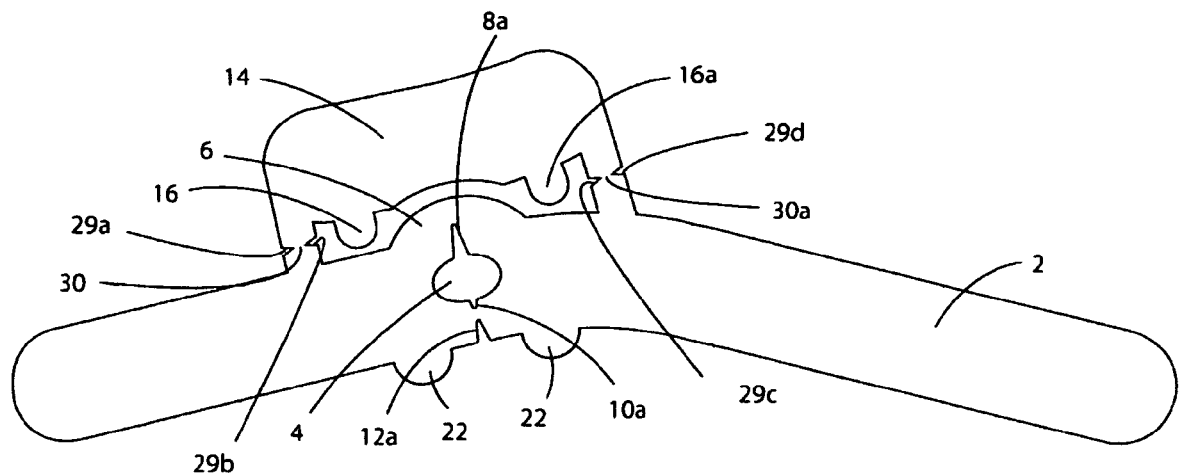
FIGS. 21A to 21C shows one unarticulated and two articulated views of a matrix with a double connected flash guard and two removal tabs and smaller semi-circular inferior guard braces.
Figure 21B:
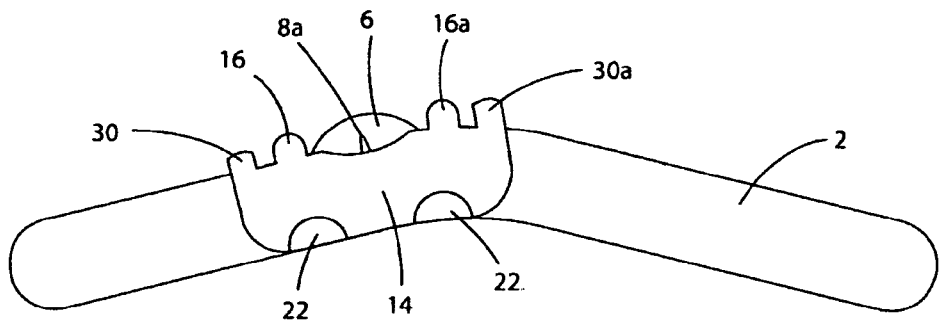
Figure 21C:
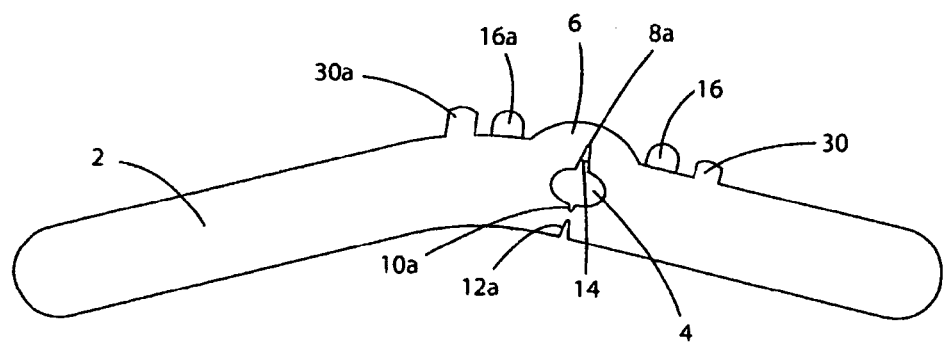

FIGS. 19A to 19C show various views of MO/DO matrix band 1, a brace 2 with a brace extrusion window 4, a flash guard 14 and smaller wing-like inferiorly positioned guard braces 22,22a. FIGS. 20A to 20C shows a matrix 1, a guard brace 22 with two severance junctions 30,30a, a flash guard 14 and two flash guard removal tabs 16,16a. FIGS. 21A to 21C shows a matrix 1, a guard brace 22 with two severance junctions 30,30a connecting the flash guard 14, two flash guard removal tabs 16,16a, and semi-circular inferiorly located braces 22.

Operation FIGS. 1A, 1B, 1C, 22-41

The manner of employing the barrier free matrix band 1 with flash guard 14 relates to the Tofflemire matrix and retaining system. First, preferably an unarticulated matrix 1 as shown in FIG. 1A is articulated. Preferably, the process of matrix articulation is accomplished by two separate folds that sandwich the flash guard 14 between the brace 2 and the guard-brace 22. Step one, the flash guard 14 is folded flush against the guard brace 22 and guard window 24 FIG. 22. The fold occurs at the mid-point or notched 28 aspect of the severance junction 30. The severance junction's 30 folding notches 29cd serve as directional folding guides to predictably position the flash guard 14 against the guard brace 22 and window 24. Step two, the guard brace 22 and articulated flash guard 14 are folded flush against the remaining brace 2 FIG. 23. This complete matrix articulation now sandwiches the flash guard 14 directly between the brace 2, brace extrusion window 4, guard brace 22 and guard brace extrusion window 24.

Figure 24:
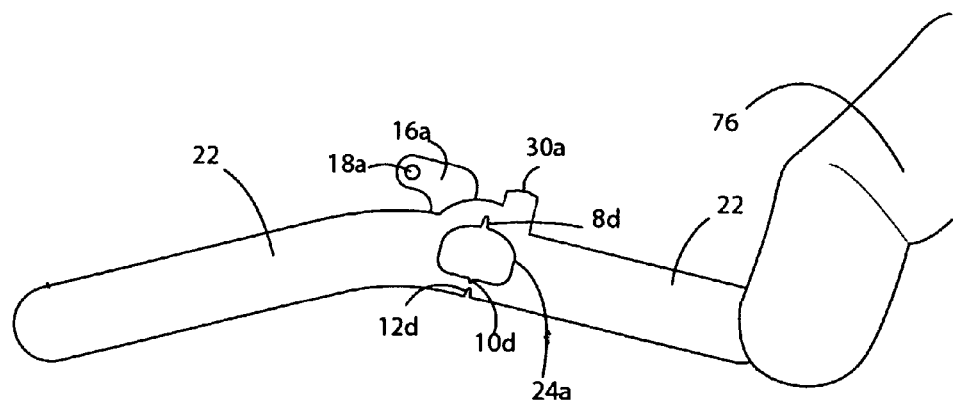
FIG. 24 shows a finger tip burnishing the articulated matrix folding points flat before insertion into a matrix retainer.
Figure 25:
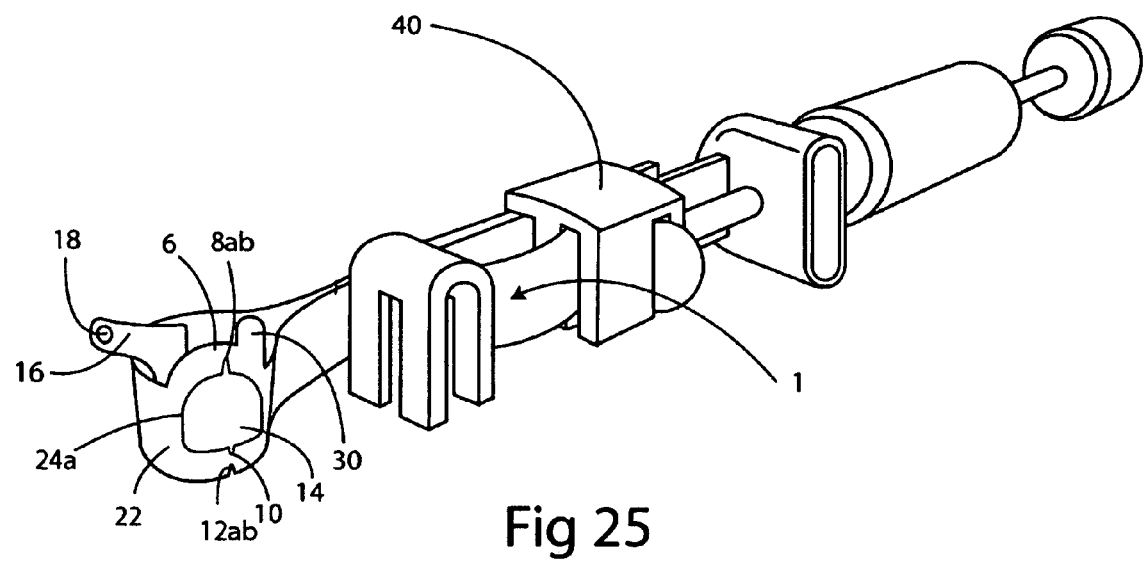
FIG. 25 shows an articulated matrix inserted into a matrix retainer.

Preferably, with a fingernail 76 or other sufficiently smooth hard object, the three folding aspects of the matrix 1 (the severance juncture 30 and two connective aspects of the brace and guard brace 22abcd) are burnished flat to promote band conformation FIG. 24. The secured flash guard 14 is now mechanically held between the brace extrusion window 4 and guard brace window 24. This flash guard division 14 serves as a temporary containing wall that will prevent the passage of a restorative material through the conjoined apertures 4a,24a. The now articulated matrix 1 is inserted into a retaining device 40 as shown in FIG. 25. The proper placement into the retainer 40 is determined by a prepared tooth's quadrant location and mesial or distal (front or back) inter-proximal position of a tooth. The inter-proximal location of a preparation always determines this specific orientation of the matrix 1 in a retainer 40, since the conjoined apertures 4a,24a and sandwiched flash guard 14 aspects of the matrix 1 must align with the preparation.

Figure 26:
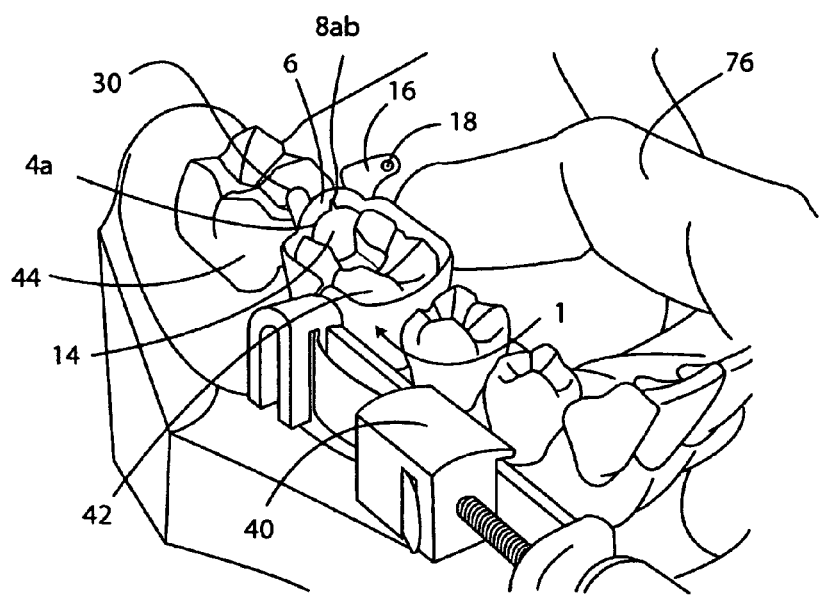
FIG. 26 shows a perspective view of the articulated matrix placed on a first prepared tooth and a second tooth.
Figure 27:
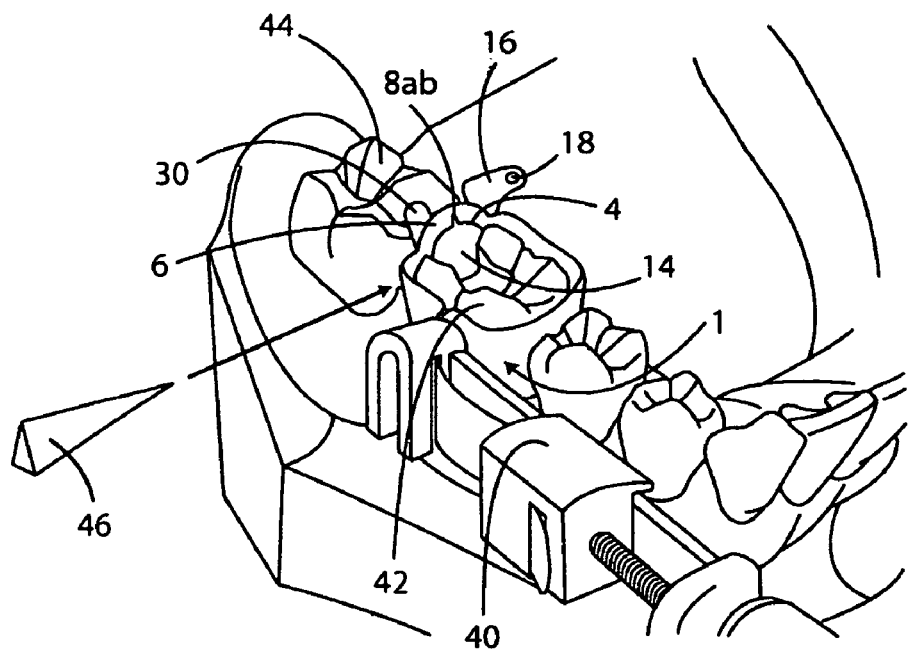
FIG. 27 shows a perspective view of the first prepared tooth and second tooth prior to wedge insertion.
Figure 28:
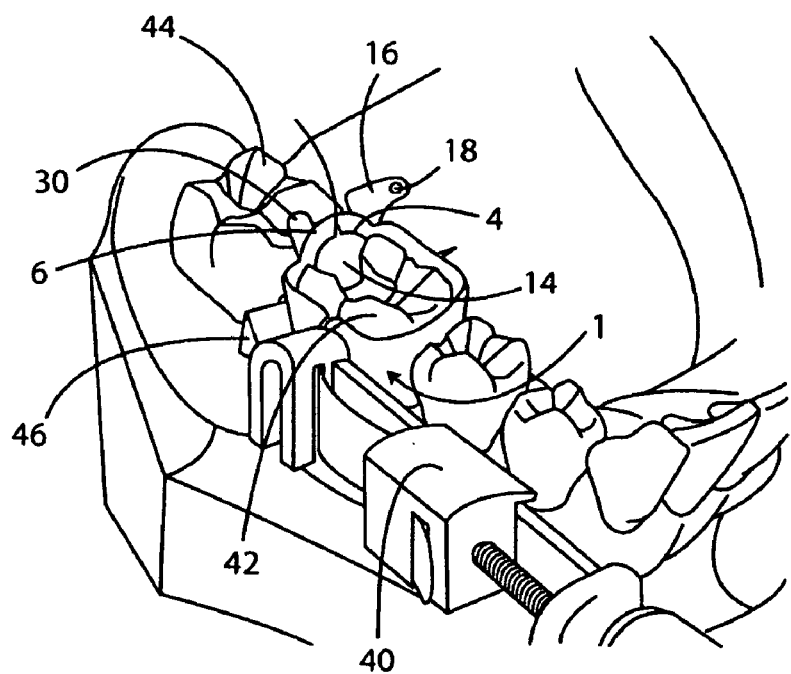
FIG. 28 shows a perspective view of the matrix, retainer and teeth after the wedge is inserted inter-proximally.
Figure 29:
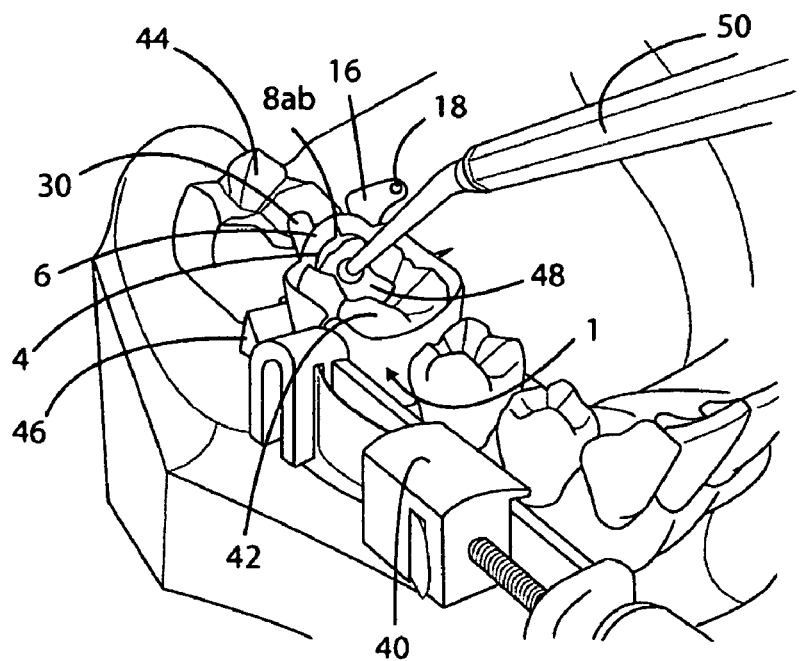
FIG. 29 shows a perspective view of composite resin being packed into a first prepared tooth against an articulated matrix's flash guard.

Preferably, the retainer 40 and matrix band 1 are now placed around a prepared tooth, positioning the windows 4a, 24a and flash guard 14 aspects of the matrix 1 with a prepped first tooth 42, as shown FIG. 26. The brace extrusion window 4a, sandwiched flash guard 14 and guard brace extrusion window 24a are positioned directly into the inter-proximal contact area between the prepped first tooth 42 and a second tooth 44. The rounded bridge's 6 top border, the medial border aspects of the removal tab 18 and severance juncture 30 (which together form a box like shape FIG. 1B and 1C approximating the general shape of a preparation) are used to guide the conjoined apertures 4a,24a into the prepared contact area of a prepped first tooth 42.

Next, the retainer 40 is tightened by an operator (not shown) to secure the matrix band 1 circumferentially around the prepped first tooth 42. To secure and seal the inferior aspects or gingival aspect of the matrix band 1 and flash guard 14, a wedge 46 is inserted into the inter-proximal space FIGS. 27-28. Next, an appropriate amount of composite resin 48 is placed into the prepped first tooth 42. The resin 48 is subsequently bulk packed thoroughly against the brace extrusion 4 or guard brace window 24 (proper placement into a retainer 40 determines which window 4, 24 is prep-side) and sandwiched flash guard 14 with a condensing instrument 50, FIG. 29. The resin 48 is packed up to and beyond the contact area of the prepped first tooth 42 and second tooth 44.

Figure 30:
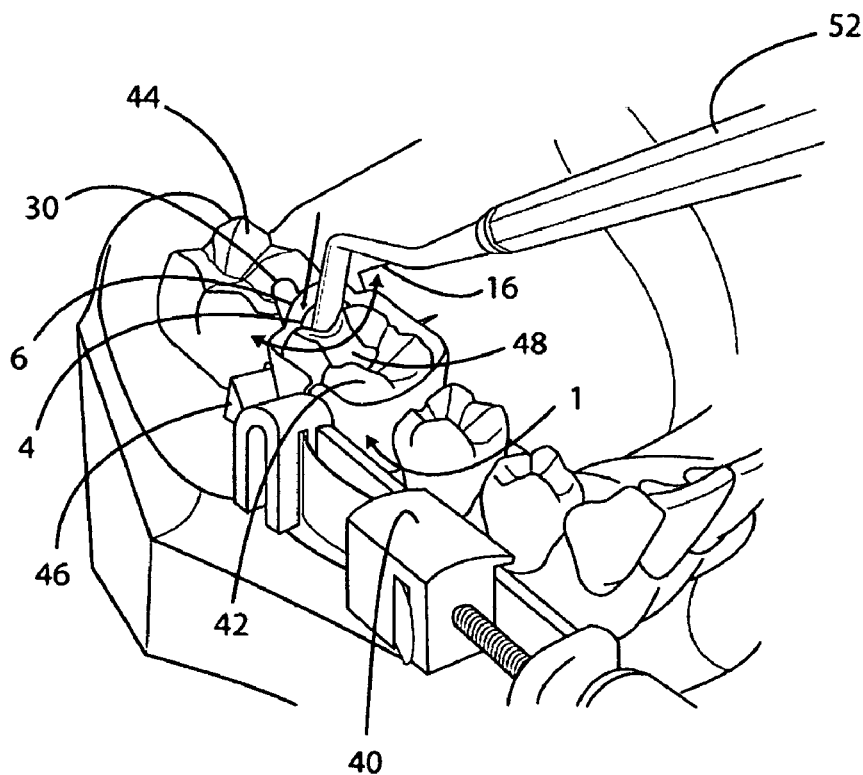
FIG. 30 shows a shaping instrument creating a marginal ridge.
Figure 31:
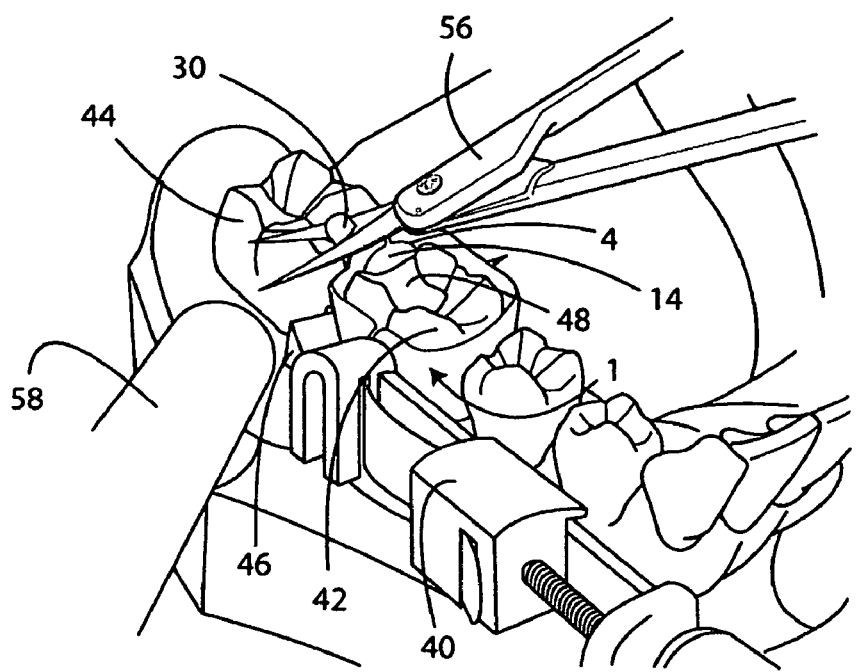
FIG. 31 shows a scissors cutting the severance junction with evacuation apparatus in place.
Figure 32:
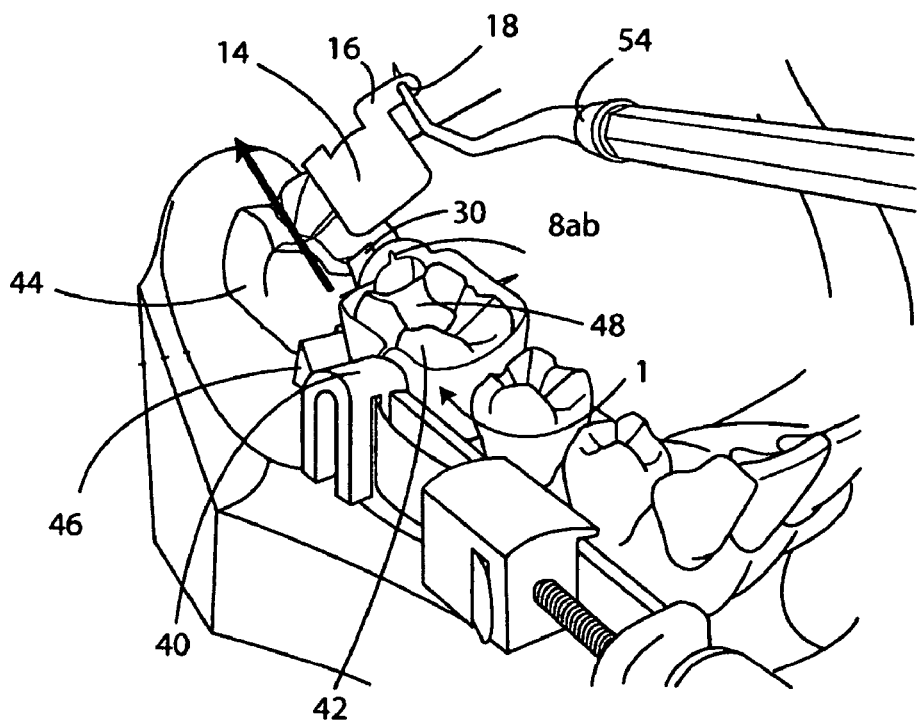
FIG. 32 shows a probe extracting a severed flash guard from the articulated matrix.
Figure 33:
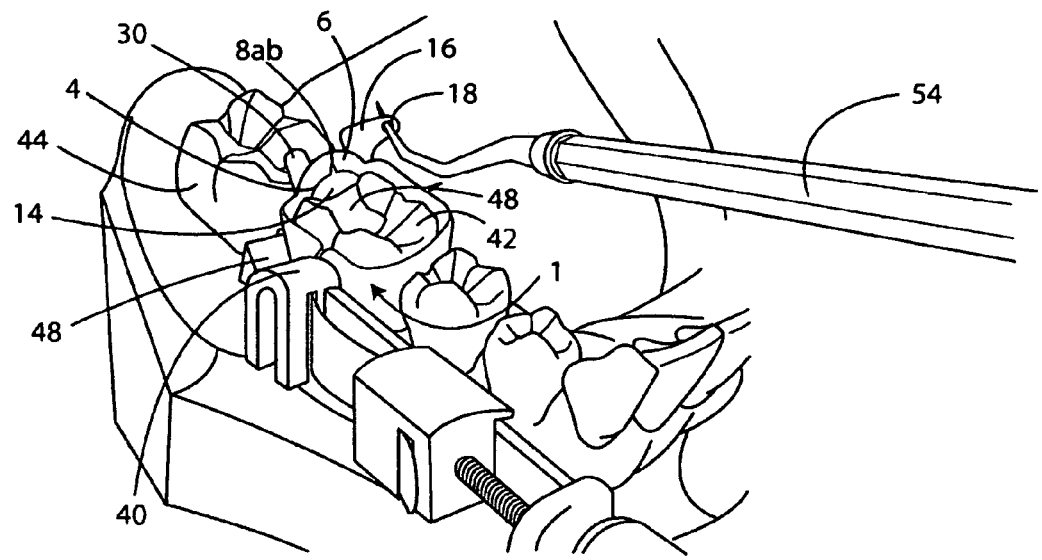
FIG. 33 shows a probe engaging the flash guard's removal aperture without pre-severing the flash guard/matrix juncture.
Figure 34:
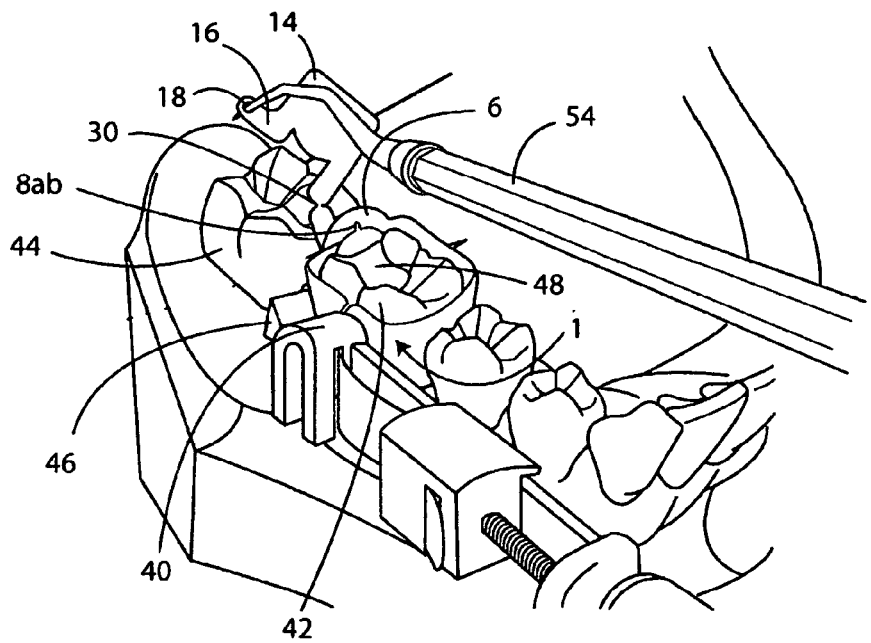
FIG. 34 shows the probe removing a flash guard with an upward motion rotational motion.

Preferably, to expedite the restorative process and facilitate the flash guard 14 removal, a shaping instrument 52 is used to contour the resin 48 in the prepped first tooth 42 FIG. 30. While sculpting the restoration, all unnecessary composite resin 48 contacting the flash guard 14 is removed. After sufficient composite resin 48 packing, a scissors 56 is used to cut the severance junction 30 FIG. 31. Prior to cutting, an evacuation apparatus 58 is placed in the mouth to catch the severed aspect of the severance junction 30 FIG. 31. A probe 54 is then inserted into the removal aperture 20 for a vertical extraction of the flash guard 14 FIG. 32. Another removal method is to not cut the severance junction 30, and to use an explorer or probe 54 to engage the removal tab's 16 removal aperture 18 FIG. 33. An upward pulling motion rotates the flash guard 14 from between the articulated matrix 2 and the inter-proximal space of a first 42 prepared and second tooth 44, FIG. 34.

Figure 35:
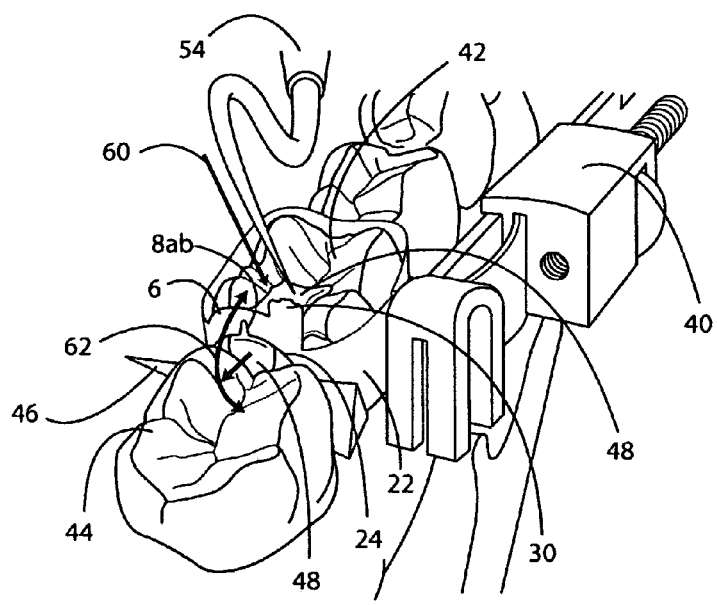
FIG. 35 shows a probe displacing composite resin.
Figure 36:
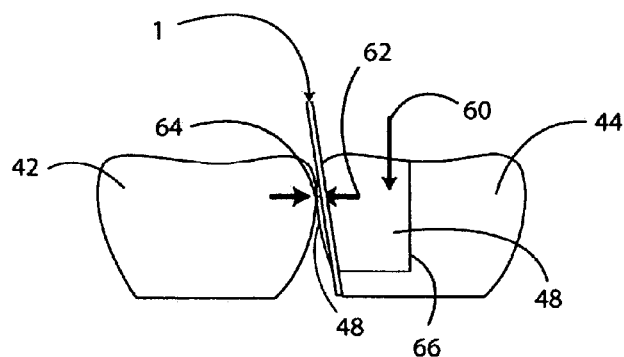
FIG. 36 shows a light pressure application displacing composite resin to create a gently contoured proximal surface with higher inter-proximal contact.
Figure 37:
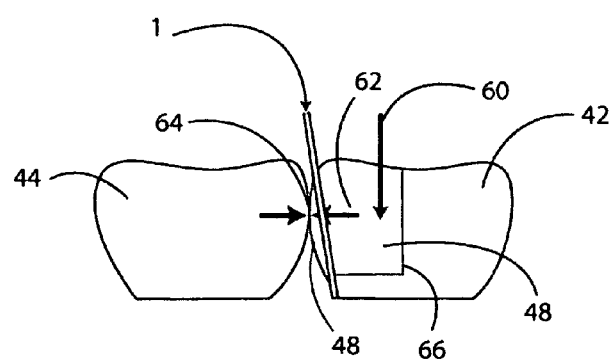
FIG. 37 shows a heavier pressure application displacing composite resin to create a pronounced proximal surface contour with lower inter-proximal contact.
Figure 38:
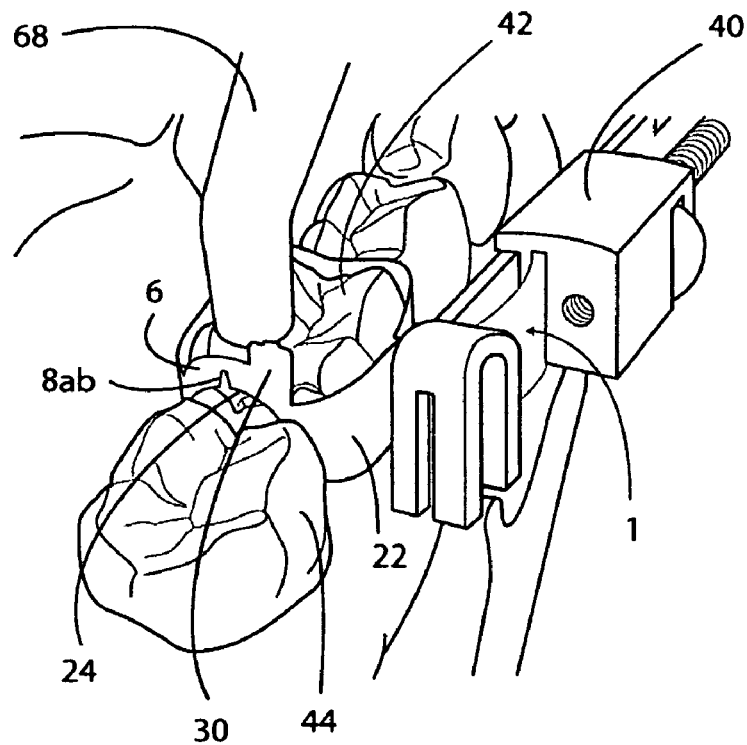
FIG. 38 shows the occlusal polymerization or light curing of composite resin.

Preferably, to ensure inter-proximal contact, a probe 54 instrument is used to penetrate the uncured resin bulk 48, FIG. 35. This probe 54 is inserted a short distance into the uncured resin 48 mass. This effects an expansive resin movement or resin displacement 62 within a prepped first tooth's 42 proximal box 66. The resin 48 is forced through the now unobstructed conjoined extrusion windows 4a.24a. This creates direct resin contact with an adjacent second tooth 44. This direct resin contact replicates a first prepared tooth's 42 original or natural contact point 60 FIGS. 36-37 (The expanding resin contacts the nearest surface which is the adjacent tooth's anatomical contact point). The expansive displacement creates curvilinear or bulging replication of natural inter-proximal tooth anatomy (natural inter-proximal contours are convexly bulged). Increased penetration or deeper probe 54 insertion in the resin mass will provide a more pronounced curvature and a lower contact point 60 with an adjacent tooth FIG. 37. Lesser resin penetration 56 and insertion results in a higher contact point 60 and a comparatively more subtle inter-proximal contour FIG. 36.

Figure 39:
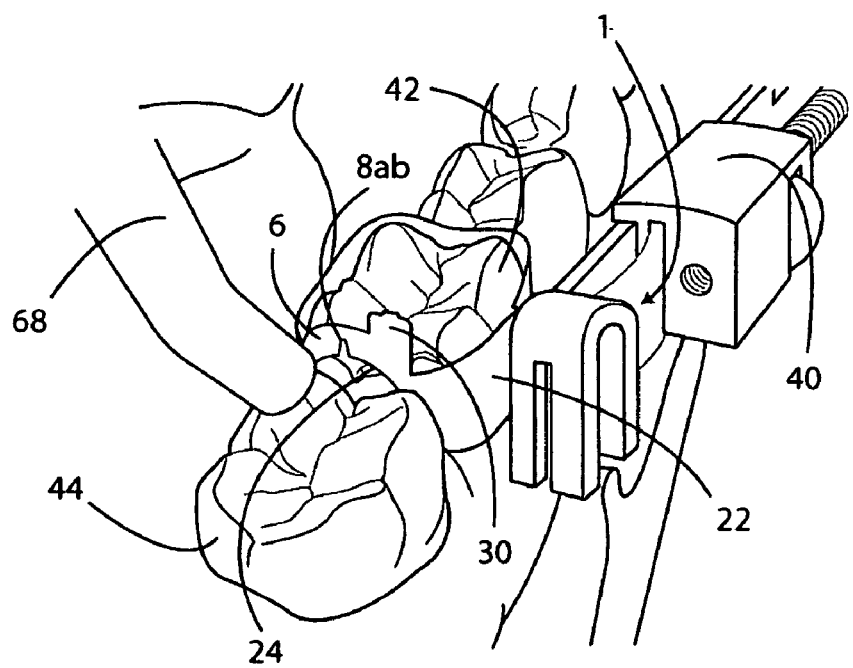
FIG. 39 shows the polymerization or light curing of composite resin through the matrix apertures.
Figure 40:
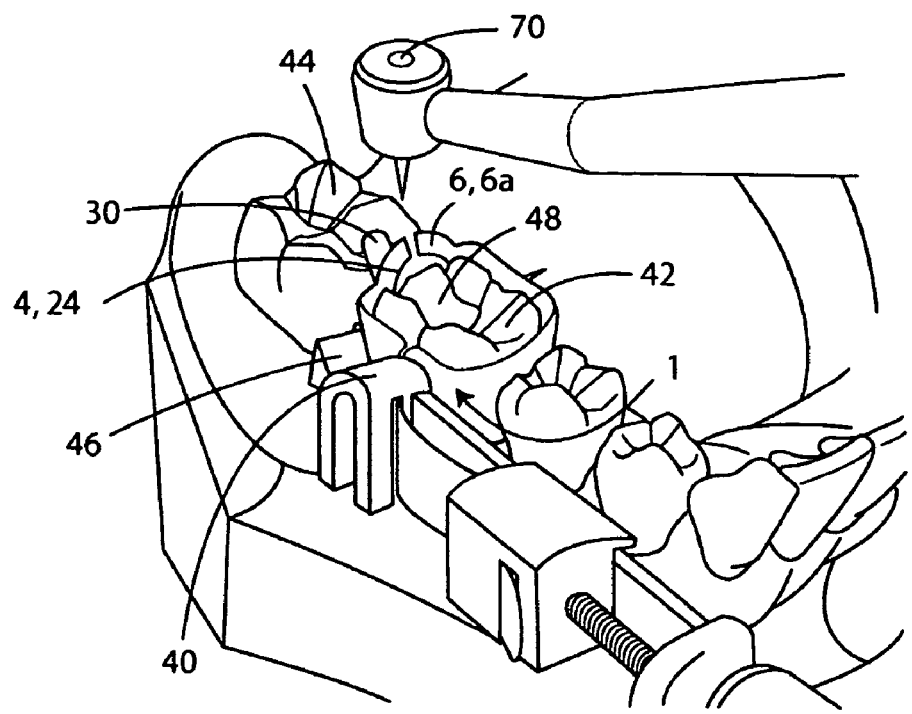
FIG. 40 shows a hand piece with diamond burr severing the rounded bridge extension to the visible notch.
Figure 41:
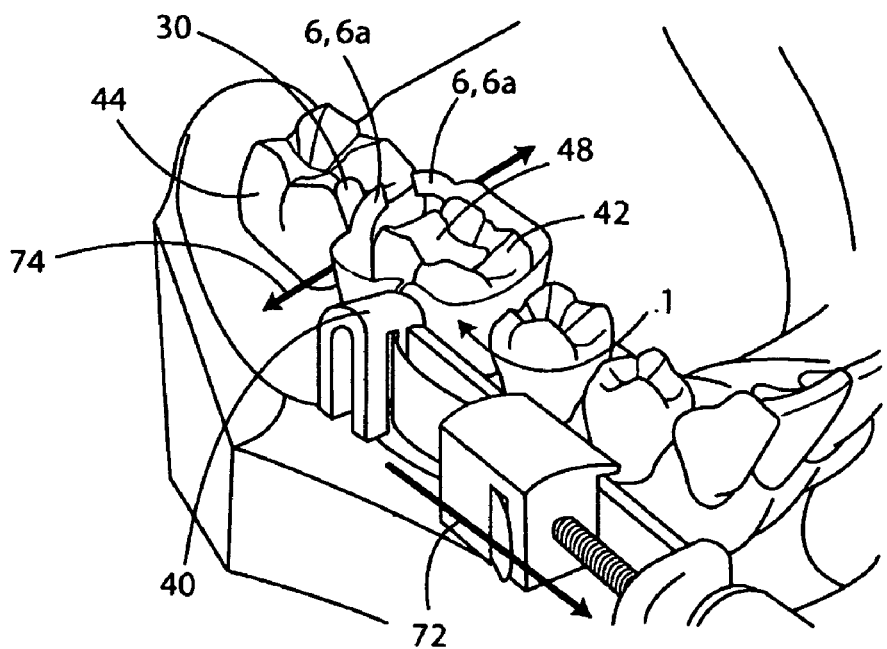
FIG. 41 shows the matrix band release after the retainer has been tightened.

Preferably, after sufficient resin displacement 62, a series of polymerizations (spectrum specific light that hardens uncured resin) are administered. The bulk resin mass 48 is cured by exposing the occlusal surface of a prepped tooth 42 FIG. 38 to an appropriate exposure of polymerizing light 68. Additional exposures of polymerizing light 68 are then administered to the inter-proximal region through the exposed conjoined apertures 4a,24a. FIG. 39. The polymerizing light will reach the bottom-most aspects of the restoration by penetration through the apertures 4a,24a and complete the curing process. After the restoration is adequately completed and polymerized, the bridge 6 is severed to the tip of the visible superior window notches 8a,b, of the brace and guard brace windows 4a,24a with a hand piece 70 and burr FIG. 40 or scissors (not shown). Next, progressive retainer tightening 72 applied by the operator (not shown) effects a buccal/lingual inferior matrix separation 74 along the inferior window notches 10a,b and gingival notches 12a,b FIG. 41. The retainer constriction splits the matrix through the conjoined apertures 4a,24a (Not shown) for easy removal.

Figure 42:
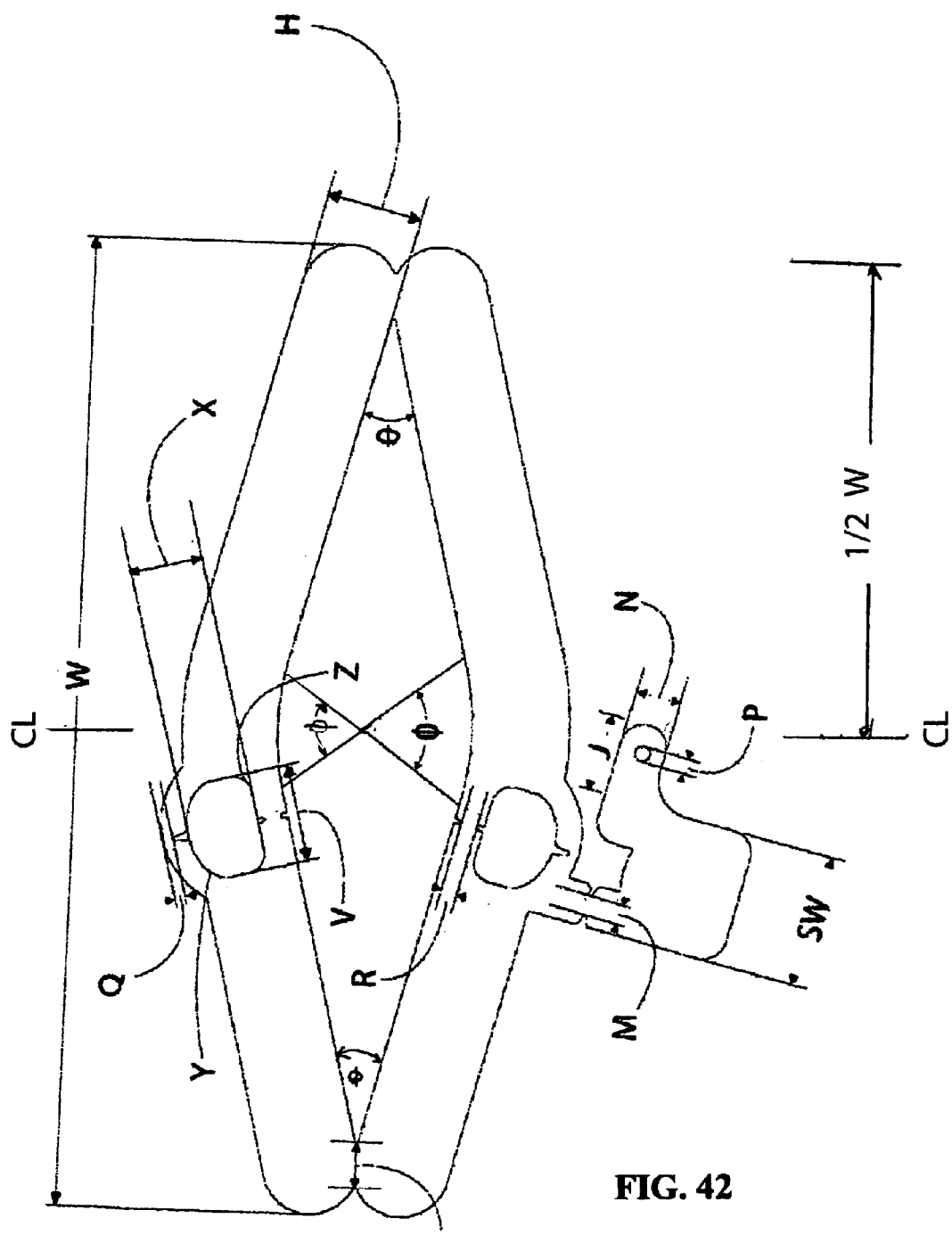
FIG. 42 (new) shows reference to table 1-Matrix Band Dimensions

For greater understanding of the nature of our invention, FIG. 42 (which is based on the view of the preferred embodiment shown in FIG. 1A) provides a key to various dimensions of the invention that are listed in Table 1 below. Of course, the dimensions shown in Table 1 are for exemplary purposes only and may be varied as necessary. Also, the key in Table 1 can be applied to corresponding multiple elements of alternate embodiments of the invention shown in FIGS. 2 through 22.

TABLE 1

Matrix Band Dimensions

|   | Preferred | Max | Min |
|---|---|---|---|
| H | 6.35 mm | 7 mm | 5.5 mm |
| J | 5.25 mm | 7 mm | 3 mm |
| K | 3 mm | 5 mm | 2 mm |
| M | 1.25 mm | 2 mm | .75 mm |
| N | 3 mm | 4 mm | 2.5 mm |
| P | 1 mm | 2 mm | .5 mm |
| Q | .75 mm | 1.25 mm | .5 mm |
| R | 1 mm | 2 mm | .5 mm |
| V | 6.5 mm | 8 mm | 5 mm |
| W | 63.5 mm | 65.5 mm | 61.5 mm |
| X | 4.75 mm | 5.75 mm | 3.75 mm |
| Y (Radius) | 6 mm | 7 mm | 5 mm |
| Z (Radius) | 5 mm | 7 mm | 4 mm |
| Theta | 28° | 30° | 26° |
| Phi | 153° | 155° | 151° |
| SW | 9 mm | 11 mm | 7 mm |
| SH | 7.5 mm | 9 mm | 6 mm |

Advantages

From the description above, a number of advantages of the barrier free matrix band with flash guard become evident.

(a) The matrix produces superior contact (b) The matrix creates anatomically correct inter-proximal anatomy (c) Use of band employs traditional techniques and armamentarium.

(d) This matrix is minimally technique sensitive.

(e) Band's design permits one-step insertion of matrix band and flash guard.

(f) The ability to have a complete barrier around the tooth permits vast restorative flexibility.

(g) The ability to remove the interim barrier will eliminate open contact.

(h) Removing the barrier is accomplished with conventional armamentarium in one easy step.

(i) This matrix band can be used with or without moisture barriers.

(j) Complete elimination of all inter-proximal flash when condensing resin.

(k) The ability to customize the degree of contact after removal of flash guard.

(l) Band's secure relationship to retainer eliminates potential for patient aspiration.

(m) Post-operative visits are minimized due to band's reliability for positive contact.

(n) Conventional retainer serves also as band remover, eliminating need for additional instrumentation.

(o) Band is compatible with dual-cured and self-cured composite resins.

Conclusion, Ramifications, and Scope

Accordingly, the reader will see that the barrier free matrix with flash guard promotes clean, predictable inter-proximal tooth contact. This is possible from the bands ability to control the direct contact of the polymerizing composite resin with the proximal surface of the adjacent tooth. The intuitive flash guard forms a temporary extrusion window barrier. This eliminates all inter-proximal flash and associated finishing complications. After the initial packing of resin and subsequent removal of the flash guard, the operator is left with a smooth, flush resin face. The operator can then customize the degree of desired contact by controlled displacement of the uncured resin bulk through the band's apertures.

This results in a positive contact that replicates the tooth's original contact point. The result is superior to other matrices in that resin displacement results in natural anatomical contours and will approximate the original contact point of the adjacent tooth. After the resin is cured, the notched release system allows for an atraumatic removal from the circumference of the tooth. This directly translates into a result that promotes predictable contact, minimal finishing, efficiency, vast restorative flexibility and lessened patient discomfort. Furthermore, the barrier free matrix with flash guard:

Allows for greater daily productivity by attaining a successful first result.

Greatly lessens chances for undesirable results by eliminating inter-proximal flash.

Allows clinicians to customize contact by applying desired displacement through the aperture.

Renders procedure as simple as the Tofflemire/amalgam standard of old

Eliminates inter-proximal irregularities, which reduces finishing time.

Dual use band design accommodates both composite resin and amalgam filling procedures.

Eliminates frustration associated with inadequate inter-proximal contact.

Is compatible with moisture control barriers.

Allows for convenient, atraumatic removal.

Is compatible with existing chair side armamentarium.

Is operator friendly and economical to use.

Presents cost effective fabrication by utilizing traditional band design.

Although the above description contains many specifications, these should not be construed as limiting the scope of the invention but merely provides presently preferred embodiments of this invention. For example, component dimensions may be altered, as need dictates. Band shape length and width can vary as future needs and procedures demand. The window's shape, size, and dimensions may be altered for optimal contact. The window can be circular or elliptical and include any degree of ellipse necessary. Geometric window apertures may also be employed. Any number of asymmetric elements may be incorporated to ensure restorative quality The bridge features are alterable to any height dimension or shape, and can be eliminated if need determines. For example, a superficial locator notch may be scored into the bridge's apex to facilitate placement of the band's extrusion window. Additionally, the separation notches are also highly variable. The separation notches may embody any shape, height or angle as determined by optimal separation. There may be any number of notches, notch combinations, and notch configurations to create optimal band strength and separation capability.

The guard brace elements can be made to any shape, size, or be positioned anywhere on the matrix as to permit optimal performance in order to promote maximum flash guard stability, band flexibility and ease of matrix articulation. The flash guard may assume any shape that is optimally secure, ergonomic, and easy to remove. Any number of guard extensions, removal tabs or other securing features may be employed to achieve an optimal restorative result. It can be coated with an appropriate lubricating material like Teflon to ease inter-proximal removal. Grooves can be incorporated into the matrix band itself that correlate with the flash guard extensions. These grooves serve as flash guard alignment guides, helping to determine exact flash guard/matrix band placement and flash guard extension folding points.

If optimal stability and band utility merit simplified designs, the flash guard extensions and removal tabs may be removed altogether. If necessary, any number of severance junctures may be incorporated to physically attach the band and flash guard. Juncture shape, size, width, height placement and thickness may be alterable to best promote flash guard stability and ease of junction severance with a drill or scissors. The physical locations of the severance juncture and removal tab may be altered to any configuration which permits intuitive severance and flash guard removal.

To note, any number of foldable extensions may be physically incorporated onto the matrix band itself if needed to facilitate flash guard articulation and security. The use of adhesive supplements or stickers may be incorporated to all appropriate aspects of the flash guard and or matrix band to ensure stability and conformational fit. The band can be made of any biocompatible metal, synthetic or other material sufficiently rigid and thin. Such material may also be used to manufacture the barrier free dental matrix band with flash guard. The MOD or bilateral versions may allow for any degree of window width and spacing to adequately permit simultaneous alignment with two or more prepared aspects of a tooth. The double-sided configuration and severance juncture may be positioned for optimal performance. The flash guard and severance juncture can take on any shape and angled relationship that will allow ease of folding and removal. The joining tab juncture may also be made to any thickness or shape with best promotes double flash guard flexibility. Lastly, the barrier free matrix band with flash guard, can incorporate any of the above attributes in any configuration, which promotes optimal restorative results, and ease of use.

INCORPORATION BY REFERENCE

The document entitled "Contact Perfect by Proxitac—Direct Contact matrix MO/DO and MOD Operation Instructions" prepared by the inventors and attached to this application is hereby incorporated by reference into this application.

Thus, the scope of the invention should be determined by the appended claims and their legal equivalents, rather than by the example given.

We claim:

1. A method for repairing the inter-proximal portion of a prepared tooth with provided restorative material, the steps of said method comprising:
    (a) encircling the tooth with a dental matrix band having an aperture over the inter-proximal portion of the prepared tooth and a cover across said aperture, said cover removably connected to said dental matrix band;
    (b) inserting the restorative material into the prepared tooth;
    (c) removing said cover;
    (d) applying sufficient compressive force on the restorative material to cause the restorative material to displace through said aperture into direct contact with an adjacent tooth's inter-proximal surface; and
    (e) removing said dental matrix band from encirclement of the tooth.

2. The method of claim 1 wherein said tooth encircling step includes providing said cover with a peninsular portion and a hole in said peninsular portion, and said cover removal step includes severing the connection between said cover and said matrix band and pulling on said cover with an instrument inserted in said hole.

3. The method of claim 1 wherein said tooth encircling step includes providing said aperture with a notch, and said matrix band removing step includes tightening the encirclement of said matrix band until said matrix band separates at said aperture notch.

4. A dental matrix band for restoring a tooth with provided restorative material, the dental matrix band comprising:
    (a) an elongated body having first and second opposing ends adapted to wrap around a tooth to be restored, said body having continuous upper and lower edges which extend between said first and second opposing ends, and an aperture formed in said body between said first and second opposing ends; and
    (b) a cover removably secured over said aperture, said cover including a tab which extends beyond said continuous upper edge of said band body, wherein said cover may be removed from said band body by pulling said tab.

5. The dental matrix band of claim 4, wherein said cover is connected to said body by a juncture integrally formed on said upper edge of said body.

6. The dental matrix band of claim 4, wherein said tab includes a hole.

7. The dental matrix band of claim 4, wherein said aperture has a periphery including at least one notch.

8. The dental matrix band of claim 4, wherein said body includes a first portion having at least one window and a second portion having at least one window, wherein said windows of said first and second portions align to form said aperture.

9. The dental matrix band of claim 8, wherein said cover is held between said first and second portions when said first and second portions are aligned to form said aperture.

10. The dental matrix band of claim 4, wherein said body includes a first portion having at least a first window and a second portion having at least a second window, and said first portion includes a left end and a right end and said second portion includes a left end and a right end, wherein said right ends and said left ends foldably connect to each other so that said first and second windows align to form said aperture.

11. The dental matrix band of claim 10, wherein said cover is connected to said body by a juncture formed on an upper edge of said first portion, wherein said juncture is foldable so that said cover is disposed between said first and second portions and over said aperture.

12. The dental matrix band of claim 4, wherein said body is comprised of a first portion containing at least one notch extending inwardly from one of said upper and lower edges, and a second portion containing at least one notch extending inwardly from one of said upper and lower edges.

13. The dental matrix band of claim 4, wherein said upper and lower edges of said body are substantially parallel.

14. The dental matrix of claim 4, wherein said aperture is spaced from said upper and lower edges.

* * * * *